(12) United States Patent
Tuseth et al.

(10) Patent No.: US 10,537,672 B2
(45) Date of Patent: *Jan. 21, 2020

(54) TRANSCATHETER DEVICE AND SYSTEM FOR THE DELIVERY OF INTRACORPOREAL DEVICES

(71) Applicant: NUHEART AS, Bergen (NO)

(72) Inventors: Vegard Tuseth, Bergen (NO); Shawn Patterson, Minneapolis, MN (US); Philip J. Haarstad, Chanhassen, MN (US)

(73) Assignee: NUHEART AS, Bergen (NO)

( * ) Notice: Subject to any disclaimer, the term of this patent is extended or adjusted under 35 U.S.C. 154(b) by 0 days.

This patent is subject to a terminal disclaimer.

(21) Appl. No.: 15/288,642

(22) Filed: Oct. 7, 2016

(65) Prior Publication Data
US 2018/0099078 A1    Apr. 12, 2018

(51) Int. Cl.
*A61M 1/12* (2006.01)
*A61M 1/10* (2006.01)
*A61M 5/142* (2006.01)

(52) U.S. Cl.
CPC ............ *A61M 1/122* (2014.02); *A61M 1/101* (2013.01); *A61M 1/1008* (2014.02); *A61M 1/125* (2014.02); *A61M 5/14276* (2013.01)

(58) Field of Classification Search
CPC .... A61M 1/1012; A61M 1/122; A61M 1/125; A61M 2025/0024; A61M 1/10; A61M 25/04; A61M 25/0113; A61M 1/1008; A61M 1/101; A61M 5/14276
See application file for complete search history.

(56) References Cited

U.S. PATENT DOCUMENTS

| 5,571,215 A * | 11/1996 | Sterman ........... A61B 17/00234 |
| | | 128/898 |
| 5,728,122 A | 3/1998 | Leschinsky et al. |
| 5,921,913 A | 7/1999 | Siess |
| 6,134,467 A | 10/2000 | Ouchi |
| 6,196,230 B1 | 3/2001 | Hall et al. |
| 6,425,916 B1 | 7/2002 | Garrison et al. |
| 7,295,878 B1 | 11/2007 | Meadows et al. |
| 7,878,967 B1 | 2/2011 | Khanal |
| 7,942,804 B2 | 5/2011 | Khaw |
| 8,157,852 B2 * | 4/2012 | Bloom .................. A61F 2/2412 |
| | | 623/1.11 |
| 8,738,147 B2 | 5/2014 | Hastings et al. |
| 9,314,556 B2 | 4/2016 | Tuseth |

(Continued)

FOREIGN PATENT DOCUMENTS

| AU | 2014201432 A1 | 10/2014 |
| EP | 2338540 A1 | 6/2011 |

(Continued)

*Primary Examiner* — Catherine M Voorhees
(74) *Attorney, Agent, or Firm* — Baker & Hostetler LLP

(57) ABSTRACT

An intracorporeal device for delivery into a patient is provided. The intracorporeal device includes a proximal end and a distal end. The distal end is detachably coupled from the transcatheter delivery device. The device relates to a transcatheter system and corresponding devices and methods of treatment, and is particularly useful for the delivery and implantation into the body of a patient of medical devices, such as mechanical circulatory support devices, but also has a wider variety of applications.

14 Claims, 16 Drawing Sheets

(56) References Cited

U.S. PATENT DOCUMENTS

| | | |
|---|---|---|
| 9,539,378 B2 | 1/2017 | Tuseth |
| 10,130,742 B2 | 11/2018 | Tuseth |
| 2001/0047150 A1* | 11/2001 | Chobotov ............. A61F 2/07 604/107 |
| 2002/0082584 A1 | 6/2002 | Rosenman et al. |
| 2002/0099396 A1 | 7/2002 | Slaker et al. |
| 2002/0173742 A1 | 11/2002 | Keren et al. |
| 2002/0173817 A1 | 11/2002 | Kletschka et al. |
| 2003/0100920 A1 | 5/2003 | Akin et al. |
| 2003/0181843 A1 | 9/2003 | Bibber et al. |
| 2003/0233143 A1 | 12/2003 | Gharib et al. |
| 2004/0006305 A1 | 1/2004 | Hebert et al. |
| 2004/0097973 A1 | 5/2004 | Loshakove et al. |
| 2004/0098081 A1 | 5/2004 | Landreville et al. |
| 2004/0236170 A1 | 11/2004 | Kim |
| 2004/0243051 A1 | 12/2004 | Monzyk et al. |
| 2005/0075696 A1 | 4/2005 | Forsberg et al. |
| 2005/0165344 A1 | 7/2005 | Dobak |
| 2005/0187425 A1 | 8/2005 | Alferness et al. |
| 2006/0079736 A1 | 4/2006 | Chin et al. |
| 2006/0089707 A1 | 4/2006 | Vassiliades et al. |
| 2006/0155158 A1 | 7/2006 | Aboul-Hosn |
| 2007/0249985 A1 | 10/2007 | Brenneman et al. |
| 2008/0195226 A1 | 8/2008 | Williams et al. |
| 2008/0300574 A1 | 12/2008 | Belson et al. |
| 2009/0088597 A1 | 4/2009 | Frazier et al. |
| 2009/0093670 A1 | 4/2009 | Annest et al. |
| 2009/0093751 A1 | 4/2009 | Tao et al. |
| 2009/0105654 A1 | 4/2009 | Kurth et al. |
| 2009/0182188 A1 | 7/2009 | Marseille et al. |
| 2009/0228078 A1 | 9/2009 | Zhang et al. |
| 2010/0191035 A1 | 7/2010 | Kang et al. |
| 2010/0268316 A1 | 10/2010 | Brenneman et al. |
| 2010/0331972 A1 | 12/2010 | Pintor et al. |
| 2011/0130619 A1 | 6/2011 | Whisenant et al. |
| 2011/0184224 A1 | 7/2011 | Garrigue |
| 2011/0196190 A1 | 8/2011 | Farnan et al. |
| 2011/0234155 A1 | 9/2011 | Chen et al. |
| 2011/0257723 A1 | 10/2011 | McNamara |
| 2011/0276075 A1 | 11/2011 | Fung et al. |
| 2011/0306916 A1 | 12/2011 | Nitzan et al. |
| 2012/0053657 A1 | 3/2012 | Parker et al. |
| 2012/0059459 A1 | 3/2012 | Asirvatham et al. |
| 2012/0139355 A1 | 6/2012 | Ganem et al. |
| 2012/0146575 A1 | 6/2012 | Armstrong et al. |
| 2012/0150259 A1 | 6/2012 | Meskens |
| 2012/0165928 A1 | 6/2012 | Nitzan et al. |
| 2012/0172654 A1 | 7/2012 | Bates |
| 2012/0172655 A1* | 7/2012 | Campbell ............. A61M 25/04 600/16 |
| 2012/0178985 A1 | 7/2012 | Walters et al. |
| 2012/0232316 A1 | 9/2012 | Nappa |
| 2012/0245649 A1 | 9/2012 | Bohori et al. |
| 2012/0259263 A1 | 10/2012 | Celermajer et al. |
| 2012/0265003 A1 | 10/2012 | DAmbrosio et al. |
| 2012/0301318 A1 | 11/2012 | Er |
| 2013/0060267 A1 | 3/2013 | Farnan et al. |
| 2013/0127253 A1 | 5/2013 | Stark et al. |
| 2013/0193914 A1 | 8/2013 | Gaddam et al. |
| 2013/0301318 A1 | 11/2013 | Asako et al. |
| 2014/0005466 A1 | 1/2014 | Crosby et al. |
| 2014/0031607 A1 | 1/2014 | Zilbershlag et al. |
| 2014/0236123 A1 | 8/2014 | Birmingham et al. |
| 2014/0287274 A1 | 9/2014 | Hwang |
| 2014/0336445 A1 | 11/2014 | Farnan et al. |
| 2015/0005570 A1 | 1/2015 | Fritz et al. |
| 2015/0119633 A1 | 4/2015 | Haselby et al. |
| 2015/0223839 A1 | 8/2015 | Spence et al. |
| 2015/0250935 A1 | 9/2015 | Anderson et al. |
| 2015/0258260 A1 | 9/2015 | Tuseth |
| 2015/0258312 A1 | 9/2015 | Tuseth |
| 2015/0335801 A1 | 11/2015 | Farnan et al. |
| 2016/0022896 A1 | 1/2016 | Burkhoff |
| 2016/0175501 A1 | 6/2016 | Schuermann |
| 2017/0000935 A1 | 1/2017 | Vasilyev et al. |
| 2017/0043077 A1 | 2/2017 | Tuseth et al. |
| 2017/0047762 A1 | 2/2017 | Tuseth et al. |
| 2017/0106176 A1* | 4/2017 | Taft ..................... A61M 27/008 |
| 2017/0189063 A1 | 7/2017 | Tuseth et al. |
| 2017/0189650 A1 | 7/2017 | Tuseth et al. |
| 2017/0196565 A1 | 7/2017 | Tuseth et al. |
| 2017/0197019 A1 | 7/2017 | Tuseth et al. |
| 2017/0216029 A1* | 8/2017 | Crowley ............. A61F 2/2418 |
| 2018/0098847 A1* | 4/2018 | Tuseth ................. A61M 1/1008 |

FOREIGN PATENT DOCUMENTS

| | | |
|---|---|---|
| GB | 2504176 A | 1/2014 |
| JP | 2008545083 A | 12/2008 |
| JP | 2012523894 A | 10/2012 |
| WO | WO199727898 A1 | 8/1997 |
| WO | WO2000027312 A1 | 5/2000 |
| WO | WO2001078580 A2 | 10/2001 |
| WO | 2005037345 A2 | 4/2005 |
| WO | WO2007003351 A1 | 1/2007 |
| WO | WO2008027869 A2 | 3/2008 |
| WO | WO2008055301 A1 | 5/2008 |
| WO | WO2008106717 A1 | 9/2008 |
| WO | WO2008134267 A2 | 11/2008 |
| WO | WO2009134471 A1 | 11/2009 |
| WO | WO2010042056 A1 | 4/2010 |
| WO | 2010121076 A2 | 10/2010 |
| WO | WO2010114666 A1 | 10/2010 |
| WO | 2010132451 A2 | 11/2010 |
| WO | WO2011011787 A2 | 1/2011 |
| WO | WO2013036588 A1 | 3/2013 |
| WO | 2013096965 A1 | 6/2013 |
| WO | WO2015075576 A1 | 5/2015 |
| WO | 2015/140179 A2 | 9/2015 |
| WO | WO2015140179 A2 | 9/2015 |

\* cited by examiner

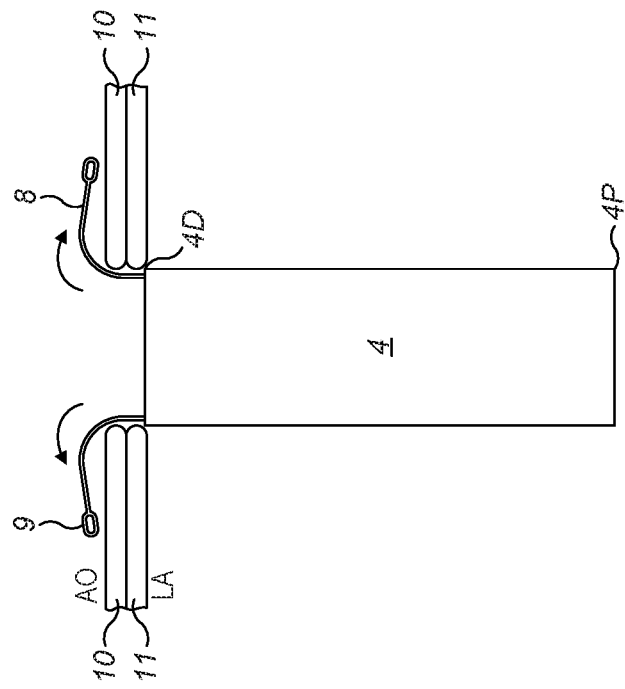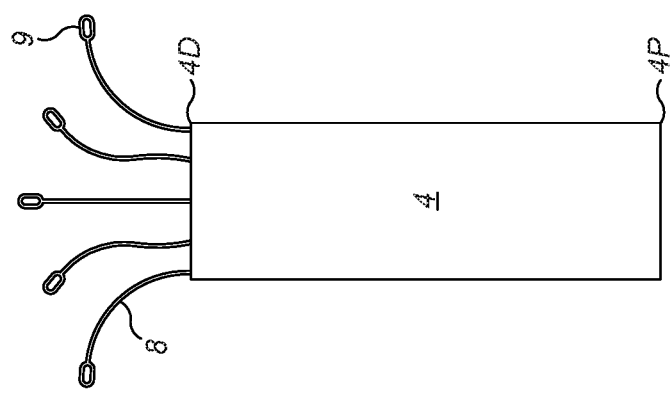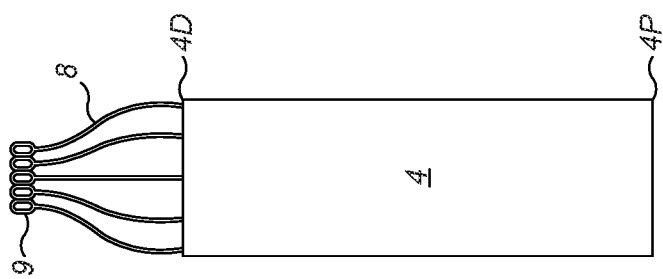

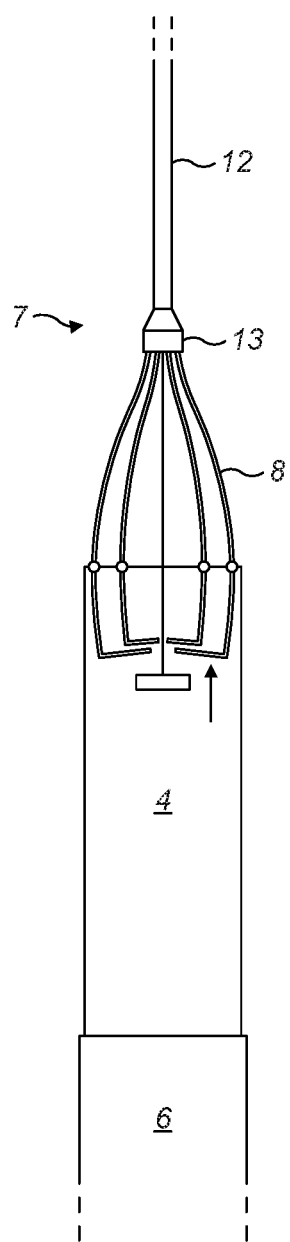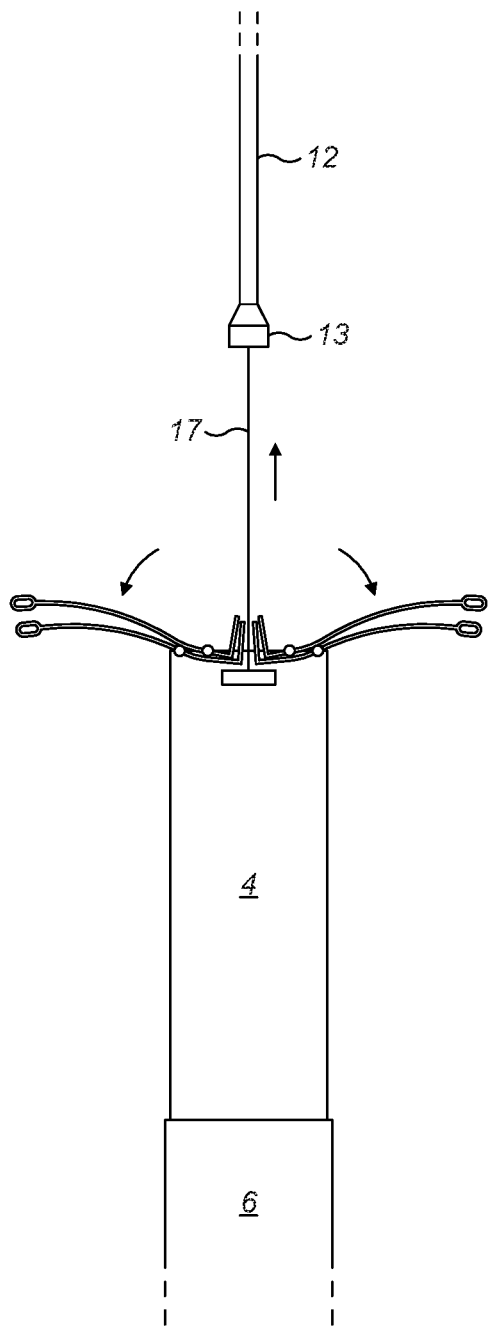
FIG. 8a
FIG. 8b

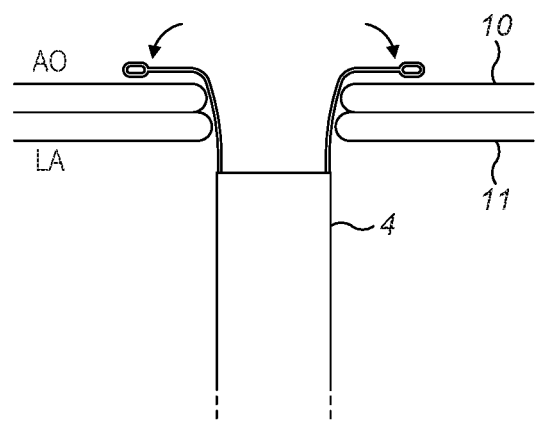
FIG. 14c

TRANSCATHETER DEVICE AND SYSTEM FOR THE DELIVERY OF INTRACORPOREAL DEVICES

FIELD OF THE INVENTION

The present invention generally relates to the field of medical devices and surgery devices. More specifically, the invention relates to a transcatheter system and corresponding devices and methods of treatment. The present invention is particularly useful for the delivery and implantation into the body of a patient of medical devices, such as mechanical circulatory support devices, but also has a wider variety of applications.

The present invention is particularly useful in the context of minimally invasive transcatheter and/or percutaneous procedures, such as those described by the Applicant in U.S. patent application Ser. No. 14/335,125, granted as U.S. Pat. No. 9,314,556, U.S. Ser. No. 14/335,142, granted as U.S. Pat. No. 9,539,378, U.S. Ser. No. 14/991,662, published as US patent application publication no. 2017-0197019, U.S. Ser. No. 14/991,675, published as US patent application publication no. 2017-0196565, U.S. Ser. No. 14/984,998, published as US patent application publication no. 2017-0189650, and U.S. Ser. No. 14/985,030, published as US patent application publication no. 2017-0189063, all of which are expressly incorporated herein by reference.

BACKGROUND

Examples of mechanical circulatory support systems (MCS) include ventricular assist devices (VADs). A VAD is a mechanical pumping device capable of supporting heart function and blood flow. Specifically, a VAD helps one or both ventricles of the heart to pump blood through the circulatory system. Left ventricular assist devices (LVAD), right ventricular assist devices (RVAD) and biventricular assist devices (BiVAD) are currently available. Also, circulatory support systems may include cardiopulmonary support (CPS, ECMO), which provide means for blood oxygenation as well as blood pumping. Such devices may be required during, before and/or after heart surgery or to treat severe heart conditions such as heart failure, cardiopulmonary arrest (CPA), ventricular arrhythmia or cardiogenic shock.

Traditionally, VADs are fitted during open-heart surgery through an incision in the chest and the procedure involves puncturing the apex of the left ventricle to re-route blood from the ventricle to the aorta through an external pump. An example of a device used in a surgical VAD is HeartMate II™. Such surgical procedures are clearly invasive and unsuitable for weaker and vulnerable patients as they involve a greater recovery time and carry the risks of infection and trauma. This is particularly the case in the treatment of children for whom existing surgical equipment and devices are comparatively bulkier and more invasive, and a reduction of the size of the equipment is often difficult if not impossible in view of the equipment and procedure involved. Furthermore, these devices require the intervention from a team of skilled surgical staff in a hospital environment and are therefore less available and costly.

More recent procedures are non-surgical and involve the insertion of a VAD through a small incision made at the groin of the patient. A popular version of such so-called percutaneous VAD is the TandemHeart™ device. A tube is introduced through an incision adjacent the groin of the patient and advanced along the femoral vein and inferior vena cava, across the intra-atrial septum and into the left atrium so that oxygenated blood from the left atrium is fed into a pumping device located outside the patient's body and recirculated through an outflow tube into the femoral artery. Although this device has shown promising results, it only provides short-term support (up to two weeks) and is unsuitable for long-term treatments. The external pump is bulky and requires the patient's immobilization for as long as the device is fitted. Furthermore, there is a risk of life-threatening infection around the groin incision, which remains open during the treatment, and of considerable bleeding from a major artery. In addition, the tube of the TandemHeart™ ends in the left atrium from which blood is pumped out and led outside the patient's body. This type of blood inlet system can potentially become hindered, if not blocked, if surrounding tissues are accidentally sucked in, thereby resulting in a loss of efficiency.

Another popular percutaneous VAD is the Impella™ device, which is inserted into the femoral artery and descending aorta. The Impella™ device comprises an elongated end, which is implanted across the natural aortic valve, with a blood inlet placed in the left ventricle and a blood outlet above the aortic valve. A pump circulates blood from the inlet to the outlet. The driveline is externalised through the femoral artery during use and the same limitations apply as with TandemHeart™ and other current percutaneous MCS systems. This device is approved to provide support for up to a week. There is therefore a need for a device with reduced risk of infection and bleeding and increased mechanical stability which can be used as part of a short-term "bridge to recovery" treatment or as a long-term treatment including patient mobilisation. In addition, the efficiency of the pump is limited because it is not possible to insert a pump of the size required to provide a suitable blood flow using percutaneous arterial access. Presently, the problem of limited pump capacity and duration with percutaneous MCS is solved either by inserting larger intracorporeal pumps surgically or by choosing an extracorporeal pump, with all the potential problems as described above.

Known mechanical circulatory support systems are positioned within the patient directly though open-heart surgery or indirectly for example using transcatheter methods in which the device is pushed to its intended position. Such a transcatheter method is described by the Applicant in PCT/EP2015/055578, expressly incorporated herein by reference. These methods involve the implantation of a guide wire extending for example from the patient's groin area, along the femoral vein, up the inferior vena cava into the right atrium, through the atrial wall into the left atrium, through the atrial roof and aortic wall into the aorta, so that the proximal end of the guide wire is outside the groin area of patient and the distal end is in the aorta. The guide wire assists in the subsequent positioning of catheters and/or sheaths through which the various devices are pushed to their target positions.

It has however been observed that the ability to accurately guide and position the devices is affected by factors such as the target position, for example, where the device is to be moved through or positioned across anatomical walls, and/or at awkward angles. There may also be some issues with the coupling between the guide wire and the device to be delivered. Ideally, the guide wire is positioned slidably and centrally within the device. Depending on the structure of the device, this central positioning is not always achievable and the device is pushed alongside the guide wire in the catheter. This potentially can result in a less accurate, and therefore less safe, device delivery process.

SUMMARY OF THE INVENTION

It is an object of the invention to at least alleviate the above-mentioned disadvantages, or to provide an alternative to existing products.

According to a first aspect of the invention, there is provided a method for the transcatheter delivery of an intracorporeal device comprising the step of establishing a device delivery pathway in a patient, wherein said device delivery pathway extends at least from an entry point into the patient to an exit point from the patient.

The present invention effectively provides a delivery system wherein the intracorporeal device and delivery devices can be manipulated and guided either from the entry point (also referred to hereinafter as "access point") or from the exit point or both the entry and exit points.

Conventional delivery systems include at least a guide wire and a delivery sheath which are inserted from an entry point into the body of the patient and advanced up to the target delivery site. The intracorporeal device is then pushed through the delivery sheath to the delivery site into its target location and position. However, the structure of the devices, the location of the target delivery site and/or obstacles in the delivery pathway may render the procedure more complicated and it becomes difficult to achieve a highly accurate delivery and implantation. In the present invention, the devices are inserted through a catheter but can be remotely manipulated from at least two different sides and angles (i.e. from the access point and the exit point) so that they can be precisely and safely guided into position.

The present method is for the delivery and/or implantation of one or more intracorporeal device, including the delivery and manipulation of an intracorporeal tool adjacent to or at the target site; the delivery, implantation positioning and/or adjustment of the medical device adjacent to or at the target site.

Preferably, the delivery pathway comprises at least one entry point and at least one exit point. Preferably, the entry point and/or the exit point is generated by a radial, subclavian, jugular, carotid and/or femoral access procedure to allow entry into and/or exit from a radial, subclavian, jugular, carotid and/or femoral vein or artery.

In other words, the entry point may be into a radial, subclavian, jugular, carotid or femoral vein or artery and the exit point may be into a radial, subclavian, jugular, carotid or femoral vein or artery. The entry point and the exit point may be located in the same region, e.g. in the groin area adjacent the femoral vein. However, in practice, optimum improvement has been observed when the entry point is remote from the exit point. For example, the entry point may be in the subclavian area, while the exit point is in the femoral area so that less pressure is exerted on the patient's anatomy during the manipulation (pushing and/or pulling) of the devices.

An initial percutaneous incision or cut may be performed adjacent the entry and/or exit point, for example in the groin area to access the femoral vein or artery, in the neck area to access the subclavian or jugular vein or artery, in the arm to access a radial artery or vein. A large vein may be preferred to a narrower artery depending on the size of the devices used in the procedure. For practical reasons, access and/or exit from the groin area of the patient may be preferred to, e.g. the neck area of the patient.

Preferably, the device delivery pathway is partly or wholly in the circulatory system. The circulatory device is ideal for this methodology as it offers a natural pathway for the delivery of medical devices, such as ventricular assist devices. Transcatheter delivery techniques are advantageous in that it allows for the safe manipulation and/or delivery of medical devices and the patient's surrounding tissues are protected from friction and trauma. The disadvantage is that the dimensions (in particular the diameter of the delivery catheter) are restricted by the dimensions of the delivery pathways (e.g. the cardio-vascular system). Consequently, the medical devices to be delivered are also limited in size and structure. The present invention is advantageous in that it enables the accurate and safe manipulation and delivery of relatively small and complex devices.

Preferably, the delivery site is located in the patient's heart. The present method can be used to deliver known intracorporeal devices to particular sensitive targets of the patient's body such as the heart, devices as those described in the Applicant's own patent publications. The implantation of such devices often involves the puncture of anatomical walls, and therefore it is crucial that the devices are implanted promptly so as to avoid any significant blood loss. On the other hand, any mis-manipulation in the circulatory system could have grave consequences for the patient. The medical practitioner using the present method can easily, accurately, promptly and safely implant the devices into their target sites.

Preferably, the delivery site is across one or more anatomical walls. The present method is particularly advantageous when applied to complex target sites and/or target sites which are difficult of access. For example, the Applicant's devices can be implanted across two anatomical walls, namely the roof of the left atrium and the atrial wall. The guiding and positioning can be complicated because of the location of the target site and the angle of implantation (not always perpendicular to the anatomical walls). It is therefore beneficial to be able to manipulate the intracorporeal device and/or the delivery device from either sides of the delivery site. The ease of manipulation and accuracy is improved.

Preferably, the present method comprises the step of positioning a sheath and/or catheter along part or whole of the device delivery pathway.

The present method is a method which involves the delivery of medical devices through one or more sheaths and/or catheters. The present description is focused on the transcatheter delivery of medical devices through punctures and/or cuts through the patient's skin. The entry point and the exit points preferably involve percutaneous openings and/or openings through one or more anatomical walls. However, it could be envisaged that the entry point and exit point are natural orifices of the patient with or without passage through one or more anatomical walls.

Preferably, the present method comprises the step of coupling the intracorporeal device to a delivery system, said delivery system being arranged and configured to extend, in use, at least to the entry point and to the exit point of the device delivery pathway.

Within the context of this invention, the expression "coupled" preferably means "physically coupled". The delivery system may be used to pushed and/or pulled along the delivery pathway using the delivery device, for example to its target delivery site. The delivery system may enable the guiding, delivery and manipulation of the intracorporeal device through the delivery pathway remotely, i.e. from beyond the entry point and the exit point of the device delivery pathway.

Most devices described in the present application are destined for permanent or semi-permanent implantation therefore, the delivery system is preferably detachable from the intracorporeal device once the latter is suitably positioned and/or implanted in the patient.

Preferably, the delivery system comprises one delivery device which extends from the entry point to the exit point of the device delivery pathway. The delivery device is preferably detachably connected to the intracorporeal device so that the delivery device can be removed from the patient's body after delivery of the intracorporeal device at the target delivery site. This entry-to-exit delivery device enables the practitioner to push the intracorporeal device e.g. from the access point and/or to pull the intracorporeal device e.g. from the exit point.

For example, the delivery device may comprise a guide wire (or equivalent cable-like or elongate element) which extends along and/or through the intracorporeal device. The guide wire may be detachably coupled to any suitable part of the intracorporeal device. In a preferred embodiment, the guide wire extends through the intracorporeal device, along the directional axis of the intracorporeal device (i.e. coaxially with the device delivery pathway). This coaxial arrangement is most advantageous in that it provides the most control of movements as the intracorporeal device can be pushed and/or pulled from its core.

In another example, the delivery device may comprise a catheter, said catheter comprising a radial separation line.

In this embodiment, the intracorporeal device is carried by and/or through a catheter which extends along the device delivery pathway. The catheter comprises a radial separation line so that the intracorporeal device can be released by separating the catheter into two parts. Each separated catheter part can be pulled out from the patient through the entry and/or the exit point. Preferably, the intracorporeal device is detachable connected to the catheter. More preferably, the intracorporeal device is positioned adjacent or at the separation line, prior to and during the delivery process. In the latter embodiment, the catheter slides through the device delivery pathway, until the separation line is aligned with the target delivery site. The catheter parts can then be separated from each other and the intracorporeal device released from the delivery catheter.

The separation line is a radial separation line, as opposed to a longitudinal separation line. Preferably, the separation line extends along the periphery of the delivery catheter so as to define a circular separation line. The separation is preferably effected by means which minimises lateral movements of the catheter when attaching/detaching the two catheter parts. A preferred separation line comprises screwing means and/or a bayonet connecting means. Alternatively or additionally, the separation line may comprise a tear line, for example a plurality of perforations and/or a catheter circumference made of thinner material thickness. natively or additionally, the separation line may comprise other securing means such as tabs, hooks, snap-fit means and the like.

Preferably, the delivery system comprises at least two delivery devices, each delivery device being coupled to an end of the intracorporeal device.

It has been observed that it is not always possible to position the guide wire coaxially with the delivery pathway, due to the presence of the components of the intracorporeal device (e.g. pump, battery or other internal components). The proposed alternative is to provide a delivery system comprising two separate delivery devices, a first delivery device extending from the entry point to the intracorporeal device (i.e. the proximal portion of the device delivery pathway) and a second delivery device extending from the device to the exit point (i.e. the distal portion of the device delivery pathway).

Preferably, the first or proximal delivery device is coupled to the proximal end of the intracorporeal device and destined to push the intracorporeal device through the delivery pathway towards the target site, and the second or distal delivery device is coupled to the distal end of the intracorporeal device and destined to pull the intracorporeal device towards the exit point.

Within the context of the invention, the terms "proximal" and "distal" are used relative to the direction of insertion of the delivery device, e.g. the proximal end is the end nearest the access point and the distal end is the end nearest to the exit point; e.g. the end of the intracorporeal device/delivery device closest to the access point is the proximal end and the end of the intracorporeal device/delivery device closest to the exit point is the distal end; e.g. the proximal portion of the device delivery pathway extends at least from the access point to the intracorporeal device; and the distal portion of the device delivery pathway extends at least from the intracorporeal device to the exit point.

In a preferred embodiment, the proximal end of the intracorporeal device is connected to the proximal delivery device extracorporeally and the distal end of the intracorporeal device is connected to the distal delivery device, extracorporeally. The distal delivery device is inserted first into the patient through the access point, followed by the intracorporeal device and the proximal delivery device. Once the intracorporeal device is safely delivered, the two delivery devices are detached and removed from the patient.

In an alternative (less preferred) embodiment, the proximal end of the intracorporeal device is connected to the proximal delivery device extracorporeally and the distal end of the intracorporeal device is connected to the distal delivery device, intracorporeally (or vice versa). The intracorporeal device is inserted through the access point and pushed through the device delivery pathway using the proximal delivery device. The distal delivery device is inserted through the exit point and pushed through the delivery pathway until it can be connected intracorporeally to the intracorporeal device.

Preferably, the delivery device comprises an elongate flexible member and means for coupling an end of said member with the intracorporeal device. The member is elongated in shape so as to fit within the device delivery pathway. In addition, the member should be flexible enough to navigate through the patient's anatomy but rigid enough so that the member can be used to push and guide the intracorporeal device through the device delivery pathway.

Preferably, the elongate flexible member comprises or consists of a delivery catheter or sheath. More preferably, the delivery catheter is destined to be used as a proximal delivery device. The delivery catheter is coupled to the proximal end of the intracorporeal device so that it is possible to push the intracorporeal device to its target delivery site.

Preferably, the elongate flexible member comprises or consists of a wire and/or cable. Preferably, the distal delivery device comprises a wire, such as a guide wire. In a preferred embodiment, the proximal delivery device comprises a catheter or a cable and the distal delivery device comprises a wire. This is because, in practice, more pushing action will be required in the proximal portion of the delivery pathway, and more pulling action will be required in the distal portion of the delivery pathway.

In another embodiment, the intracorporeal device may comprise a lead or cable, such as a cable for supplying electrical energy to the intracorporeal device. The lead or cable may be detachable or non-detachable and be used as a delivery device to push, pull and/or guide the intracorporeal device to its target position.

Preferably, the elongate flexible member comprises a portion for receiving an end of the intracorporeal device. Preferably, the elongate flexible member of the proximal delivery device comprises a portion adapted to receive the proximal end of the intracorporeal device. Preferably, the elongate flexible member of the distal delivery device comprises a portion adapted to receive the distal end of the intracorporeal device.

The end of the intracorporeal device may be the most proximal end of the device (e.g. for pushing) and/or the distalmost end of the device (e.g. for pulling). It may be a protrusion or extension from the end of the intracorporeal device. It may also be a connector (such as an expandable connector), a cap or sheath coupled to the end of the intracorporeal device, a diffusor or any other integral or detachable elements located at the end of the intracorporeal device as will be described in further details below.

In the case of a catheter as delivery device, the receiving portion may be the distal end of the catheter. In a preferred embodiment, the relative dimensions of the outer periphery of the end of the intracorporeal device and the inner circumference of the catheter are such that the catheter can grip the intracorporeal device. Preferably, the inner dimensions of the receiving portion are equal or slightly smaller than the dimensions of the end of the intracorporeal device.

In an embodiment, the inner surface of the delivery catheter comprises one or more abutments and/or protrusions arranged and configured so that an end of the intracorporeal device can sit against said abutments or protrusions. In another embodiment, it is envisaged that the catheter is detachably coupled to one or more protrusions extending from the end of the intracorporeal device so that the protrusions can fit into one or more complementary apertures or recesses in the catheter. The delivery catheter and the intracorporeal device are preferably coupled so that the intracorporeal device could also be pulled back towards the entry site if required.

In the case of a wire or cable as delivery device, the wire or cable may comprise a snare, hook, loop and/or screw means to couple with the end of the intracorporeal device. The wire or cable may comprise a cup-like, bowl-like or tubular portion capable of receiving the non-expanded connector arms, diffusor or other expandable element(s) of the intracorporeal device.

Preferably, the receiving portion comprises a means for detachably coupling with the intracorporeal device. Said detachable coupling means may for example comprise retractable tabs, screw means and other suitable means.

The means for detachably coupling the elongate flexible member with the intracorporeal device may either be secured to the delivery device and detachably coupled to the intracorporeal device or secured to the intracorporeal device and detachably coupled to the delivery device.

For example, a cap or sheath may be secured to the end of the elongate flexible member (to the distal end of a proximal delivery device or to the proximal end of a distal delivery device). The cap or sheath may be detachably coupled to the intracorporeal device so that, during the delivery process, it partially or fully covers the intracorporeal device and can be detached from intracorporeal device after successful delivery.

According to a further aspect of the invention, there is provided an intracorporeal device for delivery into a patient, wherein said intracorporeal device having a proximal end and a distal end and comprising means for detachably coupling its distal end with a transcatheter delivery device.

The present invention provides an intracorporeal device arranged and configured to be connected to a delivery device, in particular a delivery device capable of pulling the intracorporeal device into position, and to be detached after delivery, use and/or implantation.

Preferably, the intracorporeal device comprises an integrated expandable distal component, said distal component being able to change configuration from a delivery configuration to a working configuration. The delivery configuration is preferably a configuration suitable for transcatheter delivery. The delivery configuration is the configuration in which the intracorporeal device can be coupled to the delivery device; whereas in the working configuration, the intracorporeal device is detached from the delivery device.

In an embodiment, the delivery configuration may be a folded configuration and the working configuration may be a deployed configuration. However, the opposite configurations are also envisaged within the scope of the present invention, namely a deployed delivery configuration and a folded delivery configuration. Similarly, the delivery and working configurations may be retracted and extended configurations. The distal component may also be arranged and configured to change from a working position into a retrieval configuration.

The distal component may be able to change configuration from a working configuration to a retrieval configuration. In this case, the retrieval configuration is preferably a configuration suitable for transcatheter retrieval. The retrieval configuration is the configuration in which the intracorporeal device can be coupled to the retrieval/delivery device; whereas in the working configuration, the intracorporeal device is detached from the retrieval/delivery device.

Preferably, the integrated distal component is integrally formed with the intracorporeal device for ease of manufacture. In addition, the intracorporeal device with its integral distal component can be delivered and implanted safely as a single device. Alternatively, the distal component is connected to the intracorporeal device. This arrangement allows for more versatility and flexibility in the delivery and implantation procedures. In this embodiment, said connection is effected prior to insertion into the patient, and more preferably during the manufacturing process. Although the distal component can be connected to the intracorporeal device intracorporeally, it is preferred to minimise the number of manipulations within the patient.

Preferably, the distal component is movably connected to the intracorporeal device so that it can be positioned in a delivery configuration and in a working configuration. For example, the distal component can be hingedly connected to the intracorporeal device or the distal component comprises or consists of a shape-memory material, which enables the transition between a delivery configuration and a working configuration.

Preferably, in the working configuration, the integrated expanded distal component is arranged and configured to secure the intracorporeal device to one or more anatomical walls. In this embodiment, the distal component serves the dual purpose of detachably coupling the intracorporeal device to a delivery device and to secure the intracorporeal device to its target site.

Preferably, in the working configuration, the integrated expanded distal component is a flow diffusor. In this embodiment, the distal component serves the dual purpose of detachably coupling the intracorporeal device to a delivery device and to improve fluid flow. This is particularly relevant when the intracorporeal device comprises a pump. The diffuser is arranged and configured to disperse and spread the fluid exiting from the pump in order enhance fluid flow and improve control of the fluid flow.

Within the context of this invention, it is also envisaged that the diffuser be alternatively located within the main body of the pump or at its proximal. However, optimum results are achieved when the diffuser extends from or is coupled to the distal or distalmost end of the pump so that the flow of fluid is enhanced as it exits the pump. It is preferred to avoid positioning elements, such as a diffuser, within the main body of the pump, as they could potentially hinder the fluid flow and/or narrow the fluid path within the pump.

Preferably, the integrated expandable distal component comprises a plurality of expandable arms and/or blades. When the integrated expandable component is a diffusor, the general contour of the deployed arms/blades allows the flow to be enhanced. When the integrated expandable component is a connector, the arms and/or blade can deploy outwardly to lie against the anatomical wall of the second compartment (i.e. the receiving compartment).

Preferably, the integrated expandable distal component comprises a membrane extending between the arms and/or blades. When the integrated expandable component is a diffusor, then the membrane improves the diffusor efficiency. The membrane increases the surface area of the diffusor contacting the fluid and therefore increases the efficiency of the diffusor. When the integrated expandable component is a connector, the membrane may act as an additional anchor but more importantly as an additional structural support and protection for the anatomical wall(s). The membrane preferably comprises or consists of a biocompatible flexible material, which extends between the arms and/or blades (e.g. like an umbrella).

Within the context of this invention, the integral distal component may consist of a membrane (i.e. without any arms and/or blades). This provides for a flexible diffuser/connector which is unlikely to damage the surrounding tissues upon deployment. In this embodiment, the membrane may be made of a shape memory material, or of a flexible material which will adopt the working configuration owing to the fluid flowing out of the pump.

Preferably, the intracorporeal device further comprises means for pushing the integrated expandable distal component into its working configuration. It is envisaged that the integrated expandable distal component may be pushed, pulled and/or otherwise assisted into its working configuration. It is also envisaged means for pushing, pulling and/or otherwise assisting the integrated expandable distal component back into its retrieval/delivery configuration.

In an embodiment, such means comprises an inflatable balloon positioned at the distal end of the intracorporeal device. The intracorporeal device may comprise a balloon, which is in a deflated state in the delivery configuration. Upon inflation, the balloon forces the deployment of (the arms and/or blades of) the integral expandable distal component. The balloon may be positioned centrally with the arms and/or blades of the integrated expandable distal component positioned circumferentially around the balloon.

The inflatable balloon may be provided as part of the intracorporeal device or as part of a delivery device. An inflation line in fluid communication with the inflatable balloon may be provided as part of the intracorporeal device or as part of a delivery device. The inflatable balloon may be detached from the intracorporeal device and/or the delivery device after use.

A delivery device may be provided which comprises an elongate flexible member and an inflatable balloon at one end thereof, i.e. the end of the delivery device which is intended to be coupled to the intracorporeal device. The end of the delivery device comprising the inflatable balloon is coupled to the end of the intracorporeal device comprising the integral expandable component. Once the intracorporeal device is suitably positioned at the target site, the balloon is inflated so as to assist the deployment of the integral expandable component. When the integral component is suitably expanded, the delivery device (and its deflated balloon) may be detached from the intracorporeal device and removed from the patient.

In an embodiment, the coupling means may comprise an integral coupling component comprising a cap or a sheath. In this instance, the cap or sheath is integrally formed with the intracorporeal device, preferably adjacent or at the distal end of the device. More preferably, the cap or sheath is arranged and configured such that it partially or wholly surrounds a distal expandable component. One of its functions is to keep the expandable component in a non-expanded configuration. For example, if the expandable component comprises plurality of expandable arms/blades, these would be kept together in a delivery configuration under the cap or sheath. In order to release the expandable arms/blades, the cap/sheath may be removed in any suitable manner, for example torn or pulled back.

Preferably, the intracorporeal device comprises a detachable coupling component, said distal component being able to be expanded from a delivery configuration to a working configuration. In this embodiment, "detachable component" means that the component is attached to the intracorporeal device before and during the delivery process and can be detached after delivery/implantation. "Coupling component" means that the component is destined to couple the intracorporeal device to the delivery device. Thus, in this embodiment, the coupling means is not an integrated distal end, but can be detached from the intracorporeal device.

Preferably, the detachable component comprises a cap and/or a sheath, similar to the integral cap or sheath, but which in this embodiment is detachable. Upon delivery of the intracorporeal device, the cap/sheath can be detached from the intracorporeal device, thereby releasing the arms/blades into a working configuration, and be removed from the patient.

The detachable component may be attached to the intracorporeal device by any suitable means, including screw means, tabs, hooks, tearline and the like.

Preferably, the detachable coupling component is secured to the delivery device. The cap or sheath can be detachably coupled to the intracorporeal device but secured to the delivery device. Prior to or during the delivery process, the intracorporeal device is coupled to a delivery device, more specifically the distal component of the intracorporeal device is coupled to a cap or sheath. The cap or sheath is secured to or integrally formed with the delivery device. Once the intracorporeal device is suitably delivered and/or implanted, the cap or sheath is detached from the distal component of the intracorporeal device and removed by pulling the delivery device out of the patient.

In another embodiment, the detachable coupling component is secured to the delivery device. During the delivery process, the coupling component secures the intracorporeal device to the delivery device. Once the intracorporeal device is suitably positioned, the detachment of the coupling component enables the integral expandable component to deploy into its working configuration. For example, the integral expandable component may comprise a plurality of arms which are hingedly connected to the distal end of the intracorporeal device. The arms may be substantially L-shaped so that one end of the arms can be deployed outwardly, whilst the other end is arranged and configured to be interlocked into a coupling position with the delivery device or to be used as a lever by pulling the delivery device to deploy the arms into a working position.

According to another aspect of the invention, there is provided a delivery device for the transcatheter delivery of an intracorporeal device through a device delivery pathway in a patient, said delivery device comprising a catheter comprising a radial separation mechanism.

According to another aspect of the invention, there is provided a delivery device for the transcatheter delivery of an intracorporeal device through a device delivery pathway in a patient, said delivery device comprising a delivery catheter and means for detachably coupling with an intracorporeal device. In a preferred embodiment, the delivery device further comprises means for assisting the implantation of the intracorporeal device to its target delivery site. Preferably, said means comprises an inflatable balloon.

According to another aspect of the invention, there is provided a system for the transcatheter delivery of an intracorporeal device through a device delivery pathway in a patient, said system comprising an intracorporeal device as described above and a delivery device as describe above.

Within the context of this invention, the term "intracorporeal" means inside the body of a patient. For example, an intracorporeal device is a device which is destined for use and/or implantation inside the body of a patient. The term "extracorporeal" means outside the body of a patient. For example, an extracorporeal connection is a connection which takes place outside the body of the patient. It is also envisaged that a device comprises an intracorporeal part and an extracorporeal part.

The term "transcatheter" includes percutaneous, trans-atrial, trans-femoral (through the leg), trans-apical (in the chest between the ribs), and trans-aortic (in the upper chest). Preferred embodiments are percutaneous systems, devices and methods.

The term "percutaneous" is used with reference to any medical procedure where access to inner organs or other tissue is done through a puncture and/or incision through the skin (and/or the vascular system) for example into the circulatory system, as opposed to an open surgery procedure. Thus, a percutaneous method involves the percutaneous delivery of elements and may involve an incision (for example with a scalpel) to enable percutaneous delivery. In a preferred embodiment, the method provides transcardiovascular delivery of one or more devices for establishing fluid communication between anatomically separate but adjacent thoracic organs, after gaining access to the vascular system by a puncture or incision. The puncture or incision may be made at various sites where intravascular access is possible, for example in the groin, axilla, chest or abdomen.

Within the context of the invention, any of the devices and systems described herein can be used with any of the methods described herein.

The devices, systems and methods according to the present invention have been described above in connection to the delivery of an intracorporeal device to an intracorporeal target site. However, it is envisaged within the context of the invention that the devices, systems and methods according to the present invention are used for the purpose of retrieving an intracorporeal device from its implantation site.

LIST OF EMBODIMENTS

The following is a non-limiting list of potential embodiments of the present invention, set forth as embodiment groups (each an "Embodiment"). Additional embodiments of the invention are possible, as set forth throughout this specification and the drawings.

Embodiment 1

An intracorporeal device for delivery into a patient, wherein said intracorporeal device having a proximal end and a distal end and comprising means for detachably coupling its distal end with a transcatheter delivery device.

Embodiment 2

The intracorporeal device according to Embodiment 1, comprising an integrated expandable distal component, said distal component being able to be expanded from a delivery configuration to a working configuration.

Embodiment 3

The intracorporeal device according to Embodiment 2, wherein, in the working configuration, the integrated expanded distal component is arranged and configured to secure the intracorporeal device to one or more anatomical walls.

Embodiment 4

The intracorporeal device according to Embodiment 2, wherein, in the working configuration, the integrated expanded distal component is a flow diffusor.

Embodiment 5

The intracorporeal device according to any one of Embodiments 2 to 4, wherein the integrated expandable distal component comprises a plurality of expandable arms and/or blades.

Embodiment 6

The intracorporeal device according to Embodiment 5, wherein the integrated expandable distal component comprises a membrane extending between the arms and/or blades.

Embodiment 7

The intracorporeal device according to any one of Embodiments 2 to 6, further comprising means for assisting the expansion of the integrated expandable distal component into its working configuration.

Embodiment 8

The intracorporeal device according to Embodiment 7, wherein the assisting means comprises an inflatable balloon.

Embodiment 9

The intracorporeal device according to Embodiment 1, comprising a detachable coupling component, said distal component being able to be expand from a delivery configuration to a working configuration.

Embodiment 10

The intracorporeal device according to Embodiment 9, wherein the detachable component comprises a cap and/or a sheath.

Embodiment 11

The intracorporeal device according to Embodiment 9 or 10, wherein the detachable component is coupled to the delivery device.

Embodiment 12

The intracorporeal device according to Embodiment 1, comprising an integrated expandable distal component, said distal component being able to be retracted from a working configuration to a retrieval configuration.

Embodiment 13

The intracorporeal device according to Embodiment 12, wherein, in the retrieval configuration, the integrated expanded distal component is arranged and configured to release the intracorporeal device from said one or more anatomical walls.

Embodiment 14

The intracorporeal device according to Embodiment 1, comprising a detachable coupling component, said distal component being able to be retracted from a working configuration to a retrieval configuration.

BRIEF DESCRIPTION OF THE DRAWINGS

The invention will be further described with reference to the drawings and figures, in which

FIGS. 4a to 4c are schematic representations of an intracorporeal device according to the present invention;

FIGS. 8a and 8b are schematic representations of a second deployment mechanism for use in the present invention;

FIG. 13 and FIGS. 14a to 14c are schematic representations of a deployment process in a method according to the present invention.

DETAILED DESCRIPTION

The invention is described by way of examples, which are provided for illustrative purposes only. These examples should not be constructed as intending to limit the scope of protection that is defined in the claims. For example, although various aspects have been described with respect to the heart and the circulatory system, this is not intended to be limiting, and is merely performed to provide an example of implementation. Aspects disclosed herein may be utilised in any medical device implantable within the human body, for example in the cardiovascular system, respiratory system, gastric system, neurological system, and the like, some examples including implantable pumps and drug delivery pumps. As used herein, the term "means" can be equivalently expressed as, or substituted with, any of the following terms: device, apparatus, structure, part, sub-part, assembly, sub-assembly, machine, mechanism, article, medium, material, applicant, equipment, system, body or similar wording.

Figure 1:
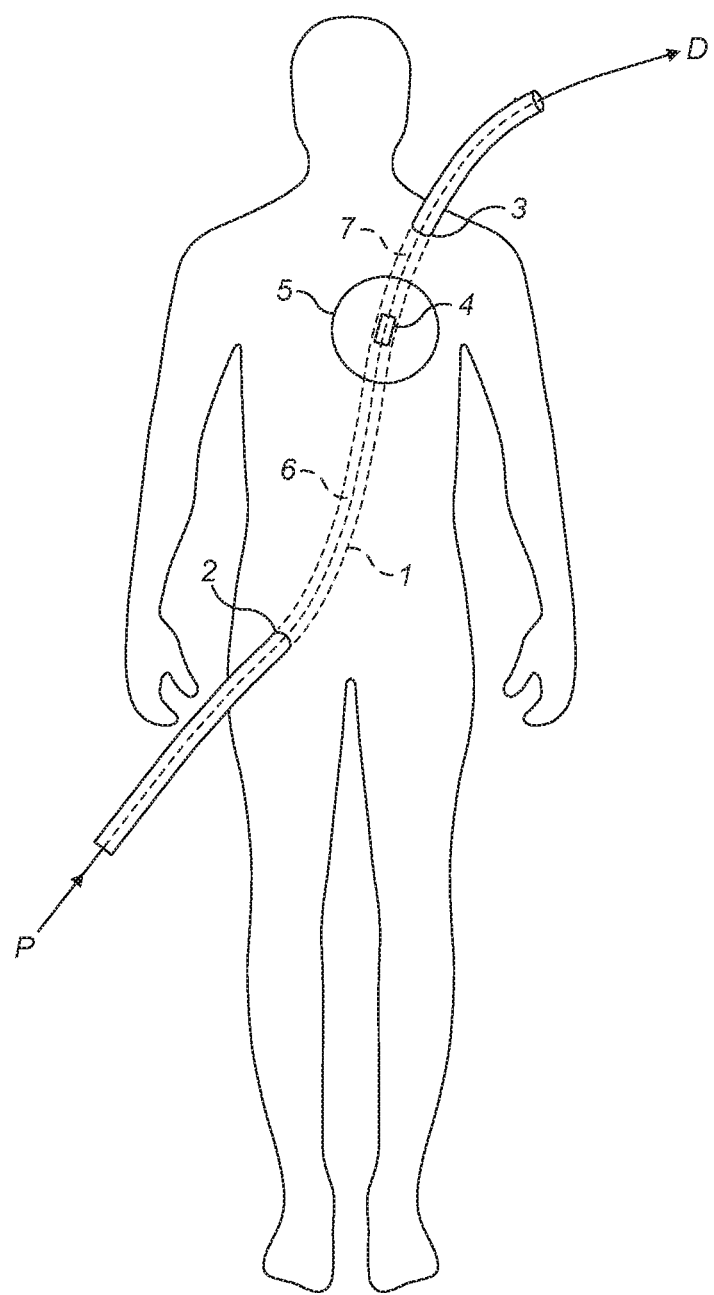
FIG. 1 illustrates a transcatheter delivery method and system according to the present invention.

Referring to FIG. 1, there is illustrated a transcatheter delivery system and method according to the present invention including a intracorporeal device delivery pathway 1 extending from an entry point 2 into a patient to an exit point 3 from the patient. In this transcatheter method, an intracorporeal device 4 is delivered to a target site 5 through a delivery catheter or sheath 6. The intracorporeal device 1 is detachably connected to a device delivery system comprising a first delivery device 6 extendable at least between the entry point 2 to the proximal end of the intracorporeal device 4 and a second delivery device 7 extendable at least between the distal end of the intracorporeal device 4 and the exit point 3. The proximal end P and the distal end D are defined relative to the direction of insertion of the delivery device, i.e. in the direction of the entry point towards the exit point.

In the embodiment shown in FIG. 1, access into the patient's body is created through a puncture or incision in the groin area and the entry point 2 is into the femoral vein or artery. Exit from the patient's body is created through a puncture or incision in the neck area with an exit point 3 from the jugular vein or in the clavicle area with an exit point 3 from a subclavian artery.

The present invention will be described in the context of the implantation of an intracorporeal device 4 for establishing fluid communication between two anatomical compartments for example the left atrium LA and the aorta AO, wherein the target implantation site is across two separate anatomical walls 10, 11, in this example the roof of the left atrium and the aortic wall. However, it is understood that the present invention can be used for different procedures at different target sites.

Figure 3:
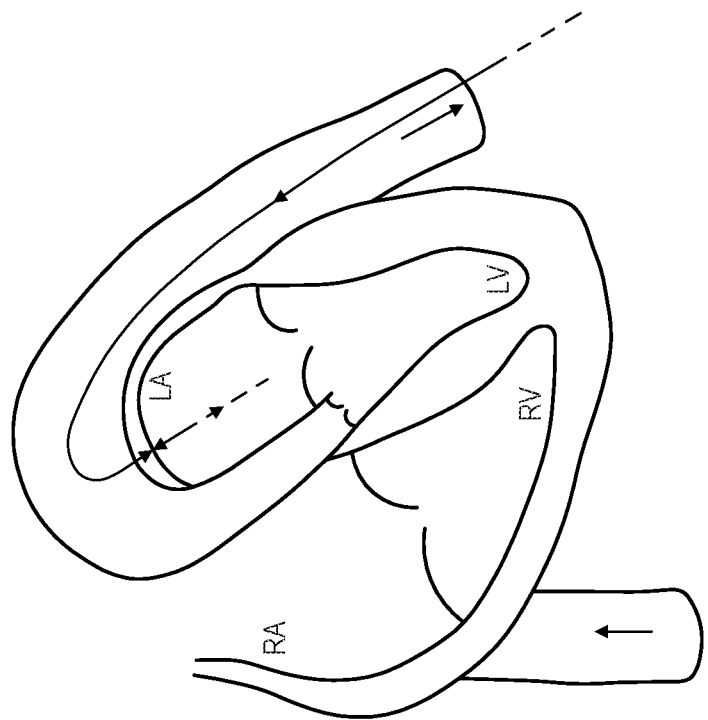
FIG. 3 illustrates a posterior device delivery pathway.
Figure 2:
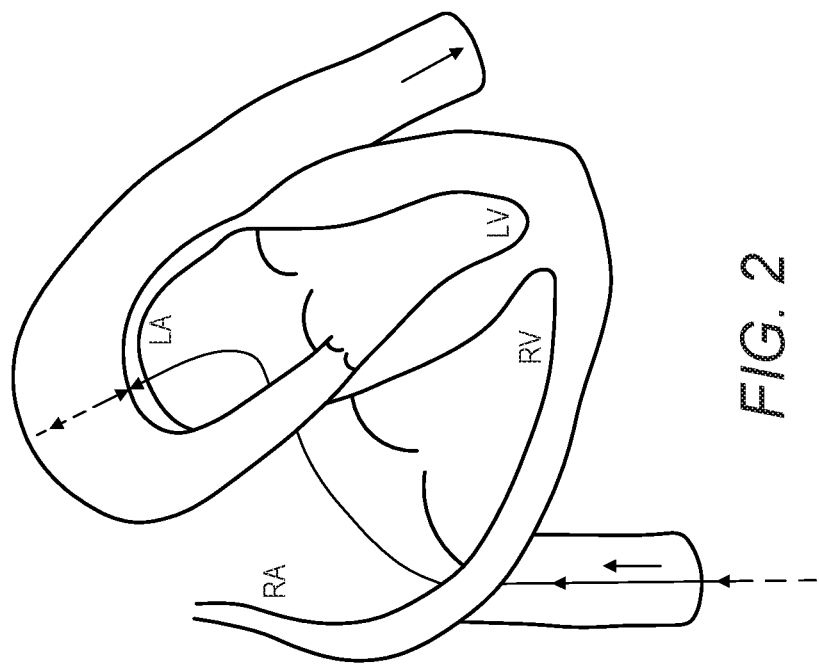
FIG. 2 illustrates an anterior device delivery pathway.

The device delivery pathway 1 extends at least between the entry point 2 and the exit point 3, but can also extend beyond the entry point 2 and the exit point 3. It is known to insert a device for intracorporeal use and/or implantation via the femoral, subclavian or jugular access. In these techniques, the device is inserted and pushed through the circulatory system up to the delivery site, for example the heart for a ventricular assist device. In the Applicant's own PCT/EP2015/055578, the devices are pushed through a puncture in the atrial septum, then delivered across the roof of the left atrium and the aortic wall in a so-called anterior delivery method (FIG. 2). It is also possible to insert a device via a posterior pathway (FIG. 3). For example, the devices can be inserted through the descending aorta into the left atrium and then delivered across the roof of the left atrium and the aortic wall.

In U.S. Ser. No. 14/991,662 and U.S. Ser. No. 14/991,675, the Applicant describes a connector comprising a neck, a first set of arms extending from a first end of the neck and a second set of arms extending from the second end of the neck. In an anterior delivery method, the delivery sheath passes through the atrial septum to the left atrium and into the aorta. In a posterior delivery method, the delivery sheath passes through the wall of the ascending aorta and the roof of the left atrium, so that the first arms deploy and lay against the roof of the left atrium as they exit the catheter, followed by the second arms against the wall of the ascending aorta. The posterior pathway is advantageous in that it presents fewer obstacles (e.g. anatomical walls to be punctured, proximity to the coronary artery and mitral and aortic valve in the anterior pathway). Depending on the structure and dimensions of the intracorporeal device 4, it can sometimes be difficult in the anterior method to accurately achieve the required positions and angles; whereas the posterior pathway provides more room to manoeuver so that larger devices can be implanted. Finally, the anterior pathway is more commonly used for physiological reasons but there is a risk of potential blood clots and strokes. This risk can be minimised by inserting posteriorly. The present invention can make use of delivery pathways such as anterior and posterior pathways.

The intracorporeal device 4 according to the present invention has a proximal end 4P and a distal end 4D, also defined relative to the direction of insertion, and means for detachably coupling its distal end 4D with a transcatheter delivery device so that the intracorporeal device 4 can be pulled in the direction of insertion. As discussed above, known methods involve pushing the intracorporeal device through a delivery sheath to the target site 5. By contrast, the method according to the present invention alternatively or additionally involves pulling the intracorporeal device 4 to the target site; and the intracorporeal device 4 according to the present invention comprises means for being pulled to the target site 5. Most preferably, the method according to the present invention enables the practitioner to both push and pull the intracorporeal device 4 (so that the intracorporeal device can be manipulated from both proximal and distal ends or from both the entry and the exit points into the patient); and the intracorporeal device 4 according to the present invention comprises means for being both pushed and pulled. This may be achieved by a number of different interconnections between the intracorporeal device 4 and the transcatheter delivery device. Within the context of the present invention, the intracorporeal device 4 may be inserted through and/or manipulated from a number of different access and exit points. The intracorporeal device 4 may be inserted forward or backward, relative to its target in-use position. Therefore, the various interconnections described herein may be used either at the distal end of the intracorporeal device 4, or both at the distal end and the proximal end of the intracorporeal device 4 (i.e. distal end 4D of the intracorporeal device 4 to proximal end of second delivery device 7; and proximal end 4P of the intracorporeal device 4 to distal end of the first delivery device 6). When the intracorporeal device 4 comprises an interconnection at its distal end and another interconnection at its proximal end, both interconnections can be the same or different. Similarly, the delivery devices described herein may be used as a first proximal delivery device 6 and/or as a second distal delivery device 7. The device delivery system described in this embodiment may be referred to as "Arterial to Venous steerable Pump Delivery" (AVPD) system.

In an embodiment illustrated in FIGS. 4a to 4c the intracorporeal device 4 comprises a housing with a proximal end 4P and a distal end 4D. The housing comprises a pump to regulate fluid flow between the left atrium LA and the aorta AO. The intracorporeal device 4 comprises a plurality of arms or blades 8 which are preferably integrally formed or secured to its distal end 4D. In a delivery (or retrieval) configuration as illustrated in FIG. 4a, the distal ends of the arms 8 are gathered together so that the arms 8 are folded and the device 4 fits in a delivery catheter. In a working configuration as illustrated in FIGS. 4b and 4c, the arms 8 are released and deployed so that the unfolded arms 8 can rest partially or wholly against an anatomical wall. In this embodiment, the arms 8 serve the dual purpose of connecting the intracorporeal device 4 to the delivery device and acting as a connector or anchor. This intracorporeal device 4 is particularly suited to a target site across one or more anatomical walls 10, 11, as the integral arms 8 can secure the intracorporeal device 4 across said anatomical walls 10, 11, and support and protect said anatomical walls 10, 11. The plurality of arms 8 may comprise a set of short arms and a set of long arms (as described in the Applicant's U.S. Ser. No. 14/991,662 and U.S. Ser. No. 14/991,675) to ensure a smooth and atraumatic release and implantation of the intracorporeal device 4.

Figure 5:
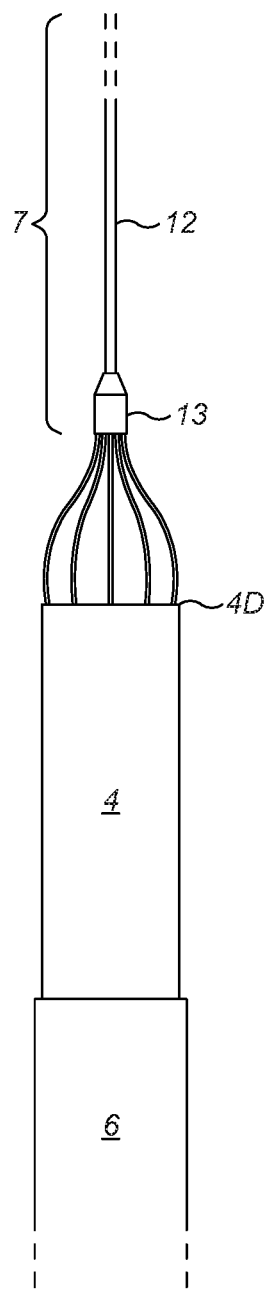
FIG. 5 is a schematic representation of an intracorporeal device and delivery devices according to the present invention.

In FIG. 5, the distal delivery device 7 intended to pull the intracorporeal device 4 comprises an elongate flexible member, in this case a wire or cable 12 and a proximal portion for receiving the distal end of the arms 8. The wire or cable 12 is rigid enough to enable accurate guiding of the intracorporeal device 4, but flexible enough to avoid injury to the patient. The receiving portion 13 is cup- or bowl-shaped. The receiving portion 13 is preferably detachably connected to the arms 8, so as to be attached during delivery and detached after successful delivery. The receiving portion 13 may comprise internal connection means for detachably connecting to the arms 4. Upon detachment of the receiving portion 13 from the arms 8, the arms 8 are released and can change from their delivery configuration to their working configuration. The arms 8 may be retained within the receiving portion 13 through tension. The arms 8 may comprise eyelets 9 to facilitate connection to the receiving portion 13. The eyelets also increase the surface area of the arms 8 and provide additional support to the anatomical walls 10, 11.

Figure 6:
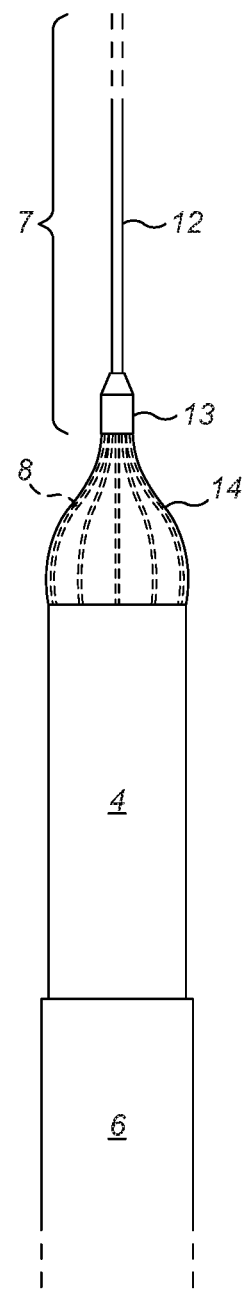
FIG. 6 is a schematic representation of an intracorporeal device and delivery devices according to the present invention.

In FIG. 6, the distal delivery device 7 comprises an elongate flexible member, in this case a wire or cable 12, a receiving portion 13 and a proximal sheath or cap 14. The sheath or cap 14 is arranged and configured to cover the folded arms 8 during the delivery process. The sheath or cap 14 is made of a bio-compatible material such as a membrane, fabric of the like. The sheath or cap 14 is secured either to the distal delivery device 7 or to the intracorporeal device 4. The sheath or cap 14 may be detachably connected to the distal delivery device 7 or to the intracorporeal device 4. For example, the sheath or cap 14 may be made of an elastic or resilient material so as to be connected to the distal end of the intracorporeal device 4; the sheath or cap 14 may be made of a tearable material or may comprise a suitably positioned tear line; the sheath or cap 14 and the distal delivery device 7 or the intracorporeal device 4 may comprise complementary detachable connections means, such as tabs, screwing means, hooks, snares and the like. The distal delivery device 7 may or may not comprise a receiving portion 13. The distal ends of the arms 8 may be detachably connected to the elongate flexible member 12 by any other suitable means.

Figure 7A:
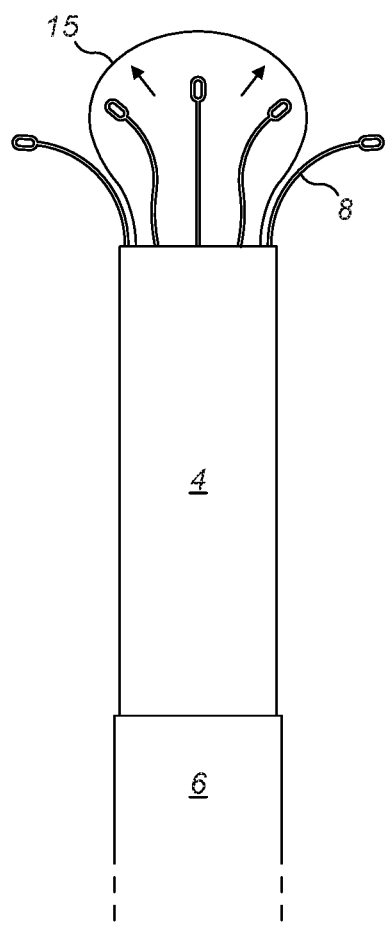
FIGS. 7a and 7b are schematic representations of a first deployment mechanism for use in the present invention.
Figure 7B:
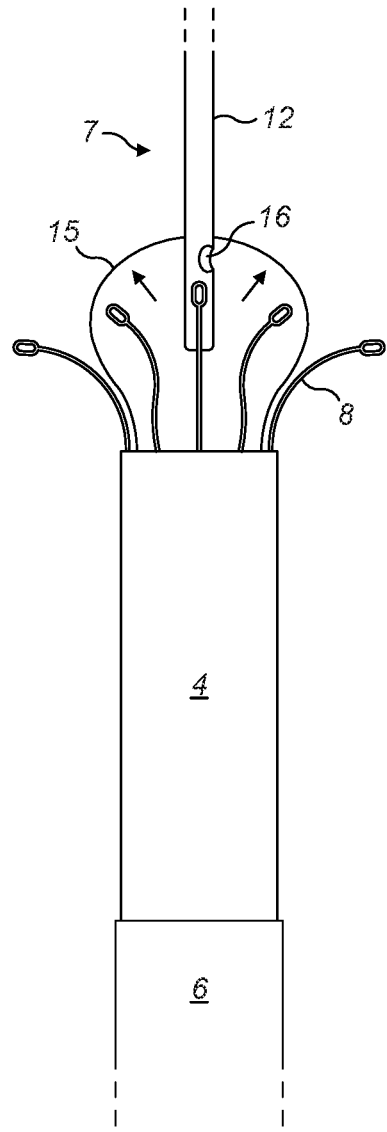

In FIG. 7a, the intracorporeal device 4 comprises an inflatable balloon 15 intended to assist the deployment of arms 8. The balloon 15 is arranged and configured so that, upon inflation, the balloon 15 pushes the arms 8 outwardly into their working configuration. The intracorporeal device preferably comprises an inflation line (not shown) for inflating the balloon 15. Alternatively, the distal delivery device 7 comprises an elongate flexible member 12 and an inflatable balloon 15 intended to assist the deployment of arms 8. The distal delivery device 7 may comprise a separate inflation line or an integrated inflation line, with an inflation port 16 into the balloon 15. It could also be envisaged that the proximal delivery device 6 comprises the inflation balloon 15 and an inflation line. It is preferred that the balloon 15 is secured to the distal or proximal delivery device 6,7 so that the balloon 15 can be detached from the intracorporeal device 14 and removed from the patient together with the delivery device after successful delivery of the intracorporeal device 4.

FIGS. 8a and 8b illustrate a different means for assisting the deployment of the arms 8. The arms 8 are hingedly connected to the intracorporeal device 4. The distal delivery device 7 comprises means 17 for pivoting the arms 8 about the hinges into their working position.

Figure 9:
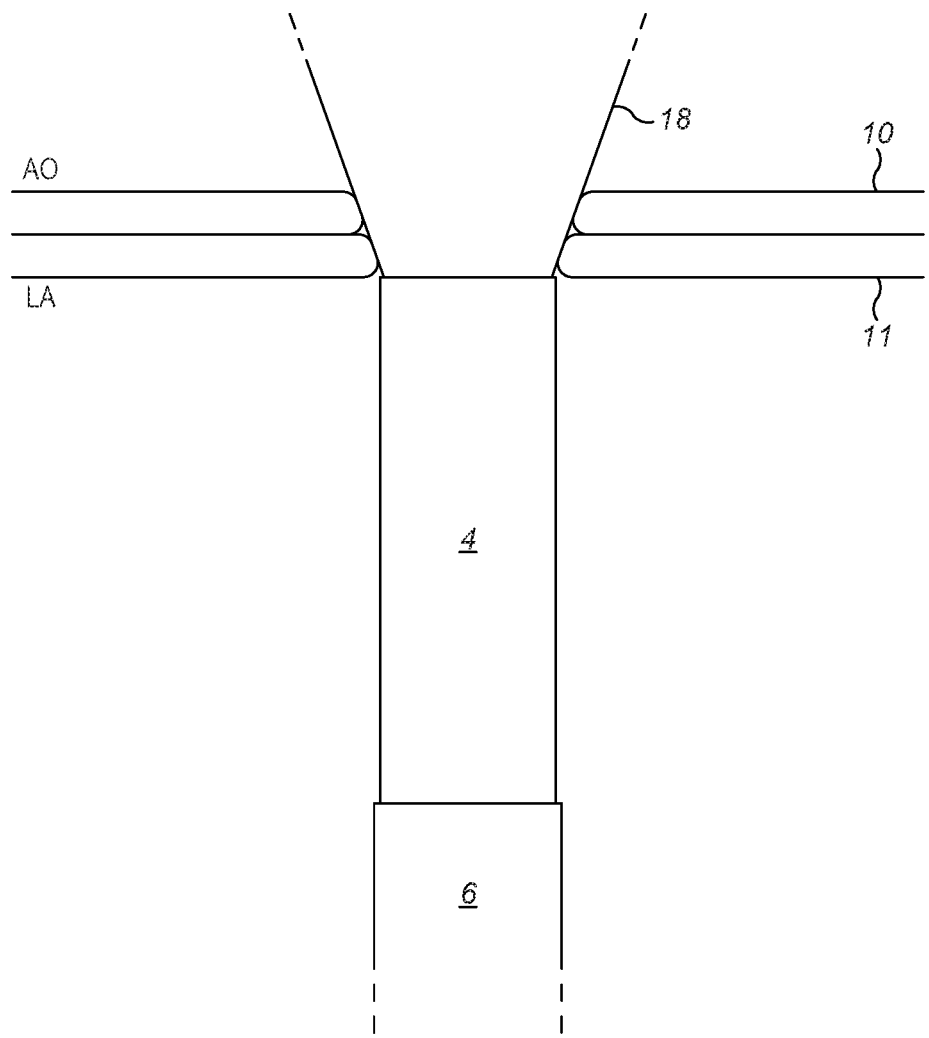
FIG. 9 is a schematic representation of an intracorporeal device and delivery device according to the present invention.

FIG. 9 illustrates an intracorporeal device 4 comprising a housing as described above and a distal flow diffusor 18. The diffusor 18 may comprise a plurality of arms or blades 8. In this embodiment, the arms 8 serve the dual purpose of connecting the intracorporeal device 4 to the delivery device and acting as flow diffusor to improve and/or enhance the fluid flow from the pump. Preferably, the diffusor 18 comprises a plurality of blades with an optional membrane extending between said blades 8. Alternatively, the diffusor 18 may comprise a membrane and be devoid of arms and blades. The diffusor 18 may be connected to the distal delivery device 7 as described above in connection to the connector arms, and be deployed in the same manner.

In the method according to the present invention, the intracorporeal device 4 need not comprise distal expandable arms or blades 8 as described above as long as it comprises means for interconnecting with a delivery device 7 so as to be pulled towards the target site 4 or towards the exit point 3. The interconnection between the intracorporeal device 4 may comprise means such as one or more tabs, screwing means, hooks, loops and/or snares and the like.

Figure 10D:
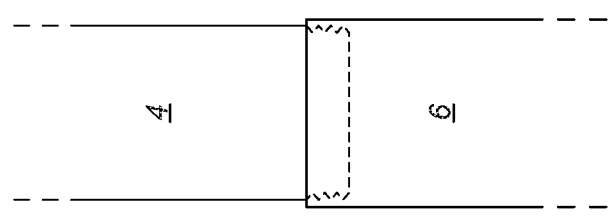
FIGS. 10a to 10d are schematic representations of delivery devices according to the present invention.
Figure 10C:
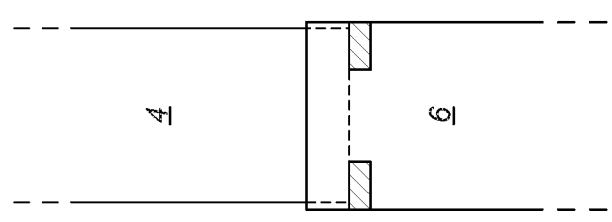
Figure 10B:
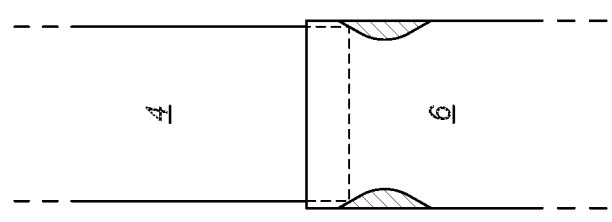
Figure 10A:
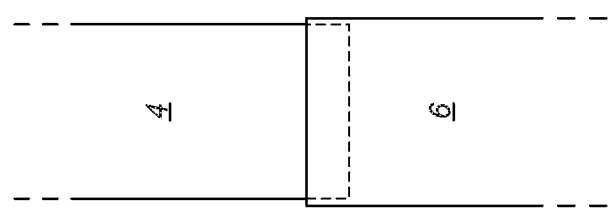

Turning now to the interconnection between the proximal end 4P of the intracorporeal device 4 and the second proximal delivery device 6, FIGS. 10a to 10d show examples of delivery devices 6 comprising a delivery catheter. The delivery catheter 6 may be made of a biocompatible flexible material. The inner diameter of the delivery catheter 6 may be equal or smaller than the outer diameter of the proximal end 4P of the intracorporeal device 4 so as to retain the intracorporeal device 4 therein. This may be achieved by using a resilient material (FIG. 10a) or by including a portion of narrower diameter (FIG. 10b). The deliver catheter 6 may comprise one or more ribs or tabs to act as an abutment to assist the pushing of the intracorporeal device 4 (FIG. 10c). The delivery catheter 6 and the intracorporeal device 4 may comprise complementary connection means, such as screwing means (FIG. 10d).

Figure 11C:
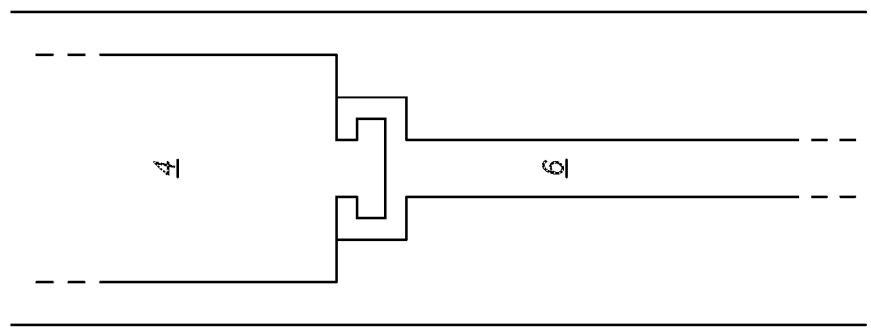
FIGS. 11a to 11c are schematic representations of delivery devices according to the present invention.
Figure 11B:
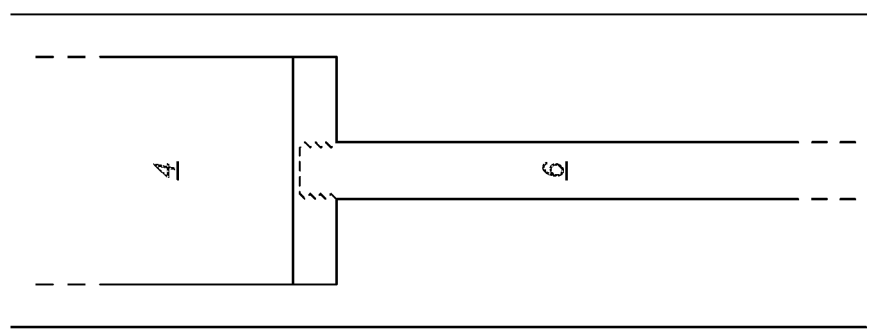
Figure 11A:
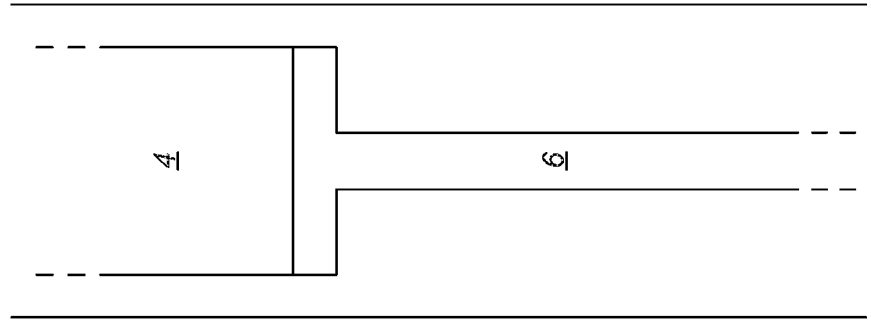

FIGS. 11a to 11c show examples of delivery devices 6 comprising a wire or cable. When the primary purpose of the delivery device 6 is to push the intracorporeal device 4, then a cable is preferred as it provides suitable rigidity and support. The cable 6 may be integrally formed or secured to the proximal end of the intracorporeal device 4 (FIG. 11a), and may for example be a cable for providing the intracorporeal device 4 with electrical energy. The cable 6 may be detachably connected to the intracorporeal device 4, for example using screwing means (FIG. 11b), tabs (FIG. 11c), hooks and the like. The wire/cable-intracorporeal device combination may be delivered through a delivery catheter or sheath. If other components or intracorporeal devices (such as driveline or battery) are required, then they may be delivered to the target site using the same delivery catheter or sheath.

Figures 12A, 12B:
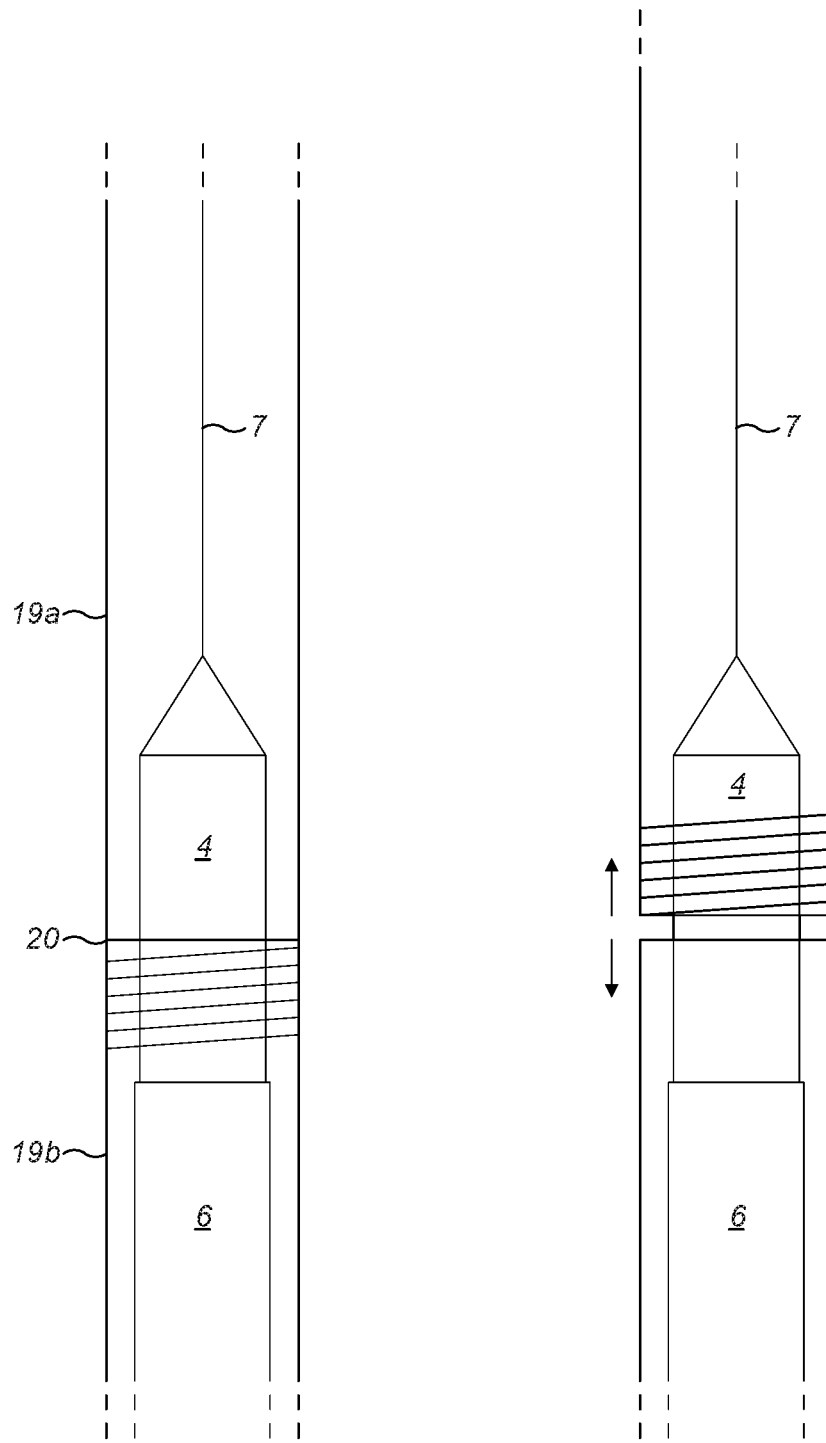
FIGS. 12a and 12b are schematic representations of a catheter or sheath with a radial separation line.

Another device 19 for use in the method according to the present invention is illustrated in FIGS. 12a and 12b. The device 19 comprises a catheter or sheath with at least one radial separation line 20 so that the catheter 19 can be separated into two portions 19a and 19b. The radial separation line 19 may comprise a tear line, complementary screwing means, complementary tabs, ribs, hooks and the like. This device 19 is useful as an outer delivery sheath, such as one used to define the device delivery pathway 6. The device 19 may alternatively be used as a device 6,7 for the delivery of intracorporeal device 4. Each portion 19a and 19b may be detachably connected to the intracorporeal device 4 during the delivery process and disconnected after successful delivery.

Within the context of the invention, it is envisaged that either or both delivery devices 6,7 comprise means for remotely controlling the interconnection between the delivery device(s) and the intracorporeal device 4, to remotely guide and manipulate the intracorporeal device and/or to remotely guide and manipulate the end of the delivery device(s) inside the patient.

A method according to the present invention will now be described by way of example with reference to the anterior delivery and implantation of an intracorporeal device 4 for fluid connection between the left atrium LA and the aorta AO, with target implantation site across the roof of the left atrium and the aortic wall.

The first step is the insertion of a guide wire, which can be carried out by means known in the art. An incision or puncture is performed in the groin area of the patient, adjacent the femoral vein or artery. A guide wire is advanced along the femoral artery and up the inferior vena cava and enters the right atrium. A septal puncture between the right and left atrium can also be carried out by means known in the art. A puncture device such as one described in the Applicant's PCT/EP2015/055578 is used to push the left atrium and the aortic wall against each other and puncture both walls.

Known visualisation techniques such as X-ray, fluoroscopy, echocardiography and ultrasound techniques may be used. The inventors have also discovered that techniques for mapping the puncture site can be crucial in hindered and complex target sites such as the heart. This is particularly true when the target site is across two separate anatomical walls, as the puncture wire have a tendency to deflect from the wall surface is not positioned centrally and at a specific angle. The preferred mapping techniques in the context of the present invention include Intra-Cardiac Echochardiography techniques (ICE), Trans-Cardiac Echochardiography (TCE), Trans-Thoracic Echochardiography (TTE), Computer Tomography (CT), Magnetic Resonance Imaging (MRI) techniques.

Any of the delivery devices and/or delivery sheath can comprise magnet or magnetic means to accurately position the devices and surround the puncture site. For example, the distal end of the proximal delivery device in the first anatomical compartment and the proximal end of the distal delivery device in the second anatomical compartment may have magnetic coupling or other coupling means so that the two ends meet accurately with each other on either side of the anatomical walls to be punctured.

Once the punctures have been carried out, the guide wire is advanced into the aorta into a subclavian artery where a further puncture is made in the arterial wall. The guide wire exits the patient's body in the patient's neck area. Using methods and devices known in the art, an outer delivery sheath is positioned around the guide wire and along the device delivery pathway 6. In a preferred embodiment, the outer delivery sheath is a device 19 as shown in FIG. 12 and the radial separation line 20 is positioned adjacent the target site 5, in this case the roof of the left atrium and the aortic wall. The delivery pathway 6 between an entry point 2 and exit point 3 is established.

Outside the patient's body, the intracorporeal device 4 is prepared for insertion. The distal end 4D of the intracorporeal device 4 comprises a plurality of arms 8. The distal delivery device 7 comprises a wire 12 and a tubular receiving portion 13. The distal end of the arms 8 are received in the receiving portion 13 of a distal delivery device 7. In a preferred embodiment, a wire 21 comprising an inflatable balloon 15 is pre-loaded into the distal delivery device 7. The inflatable balloon 15 comprises means for detachably connecting with the distal end of the intracorporeal device 4, in this case screw means 22. The proximal delivery device comprises a catheter 6. The distal end of the catheter is connected to the proximal end 4P of the intracorporeal device 4 for example by means of complementary screw means. The intracorporeal device 4 is connected to both delivery devices 6,7 and ready for insertion.

The wire 12 of the distal delivery device 6 is inserted first through the entry point 2 into the outer delivery sheath 19 and pushed forward until it exits the patient at exit point 3. The intracorporeal device 4 is advanced along the delivery pathway 6 through the outer sheath 19 by pushing using the proximal delivery device 6 and/or pulling using the distal delivery device 7, until it reaches the target delivery site 5.

In an alternative embodiment, the intracorporeal device 4 is connected (extracorporeally) to the proximal delivery device 6, inserted through the entry point 2 and advanced along the delivery pathway 6 to the target delivery site 5. The distal delivery device 7 is inserted through the exit point 3 and advanced along the delivery pathway 6 to the target delivery site 5, where it is intracorporeally connected to the intracorporeal device 4. However, the extracorporeal connection of the intracorporeal device 4 to both distal and proximal delivery devices is preferred, as it minimised the number of manipulation within the patient, and therefore the risk of accidents.

Figure 13:
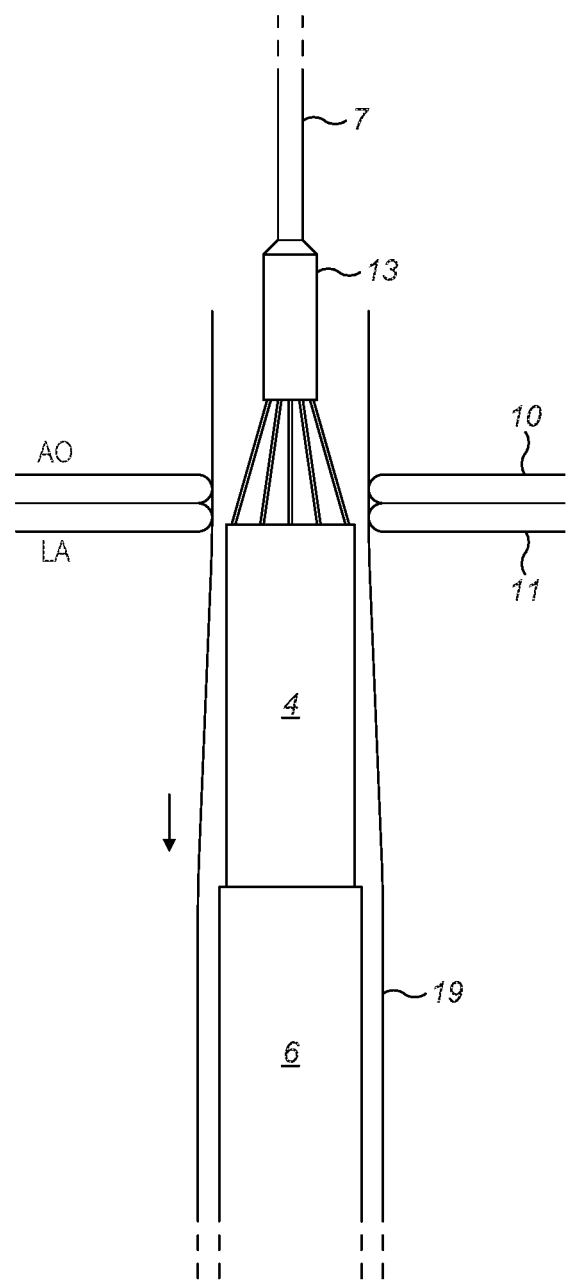

The intracorporeal device 4 is accurately and safely guided and positioned across the anatomical walls (i.e. roof of the left atrium and aortic wall) using the distal delivery device 7 and the proximal delivery device 6. If the outer delivery sheath is a sheath as shown in FIG. 12, then sheath distal and proximal portions 19a and 19b are separate from each other and the distal portion 19a is pulled out of the patient's body. If the outer delivery sheath is a standard one-piece delivery sheath, then it is pulled back towards the entry point 2, until its distal end is adjacent the target delivery site 5. The intracorporeal device 4 is now ready for implantation (FIG. 13).

Figure 14A:
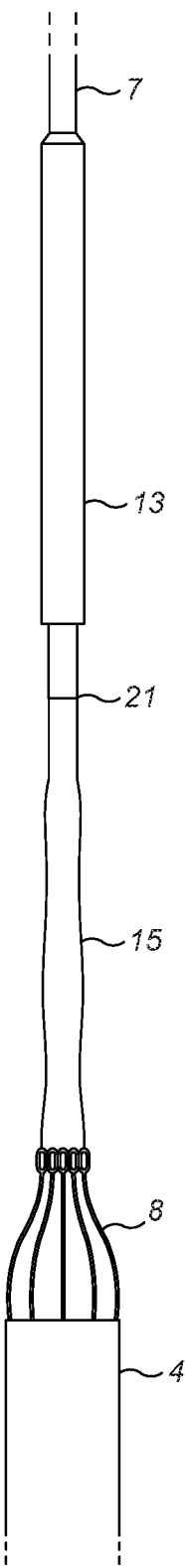
Figure 14B:
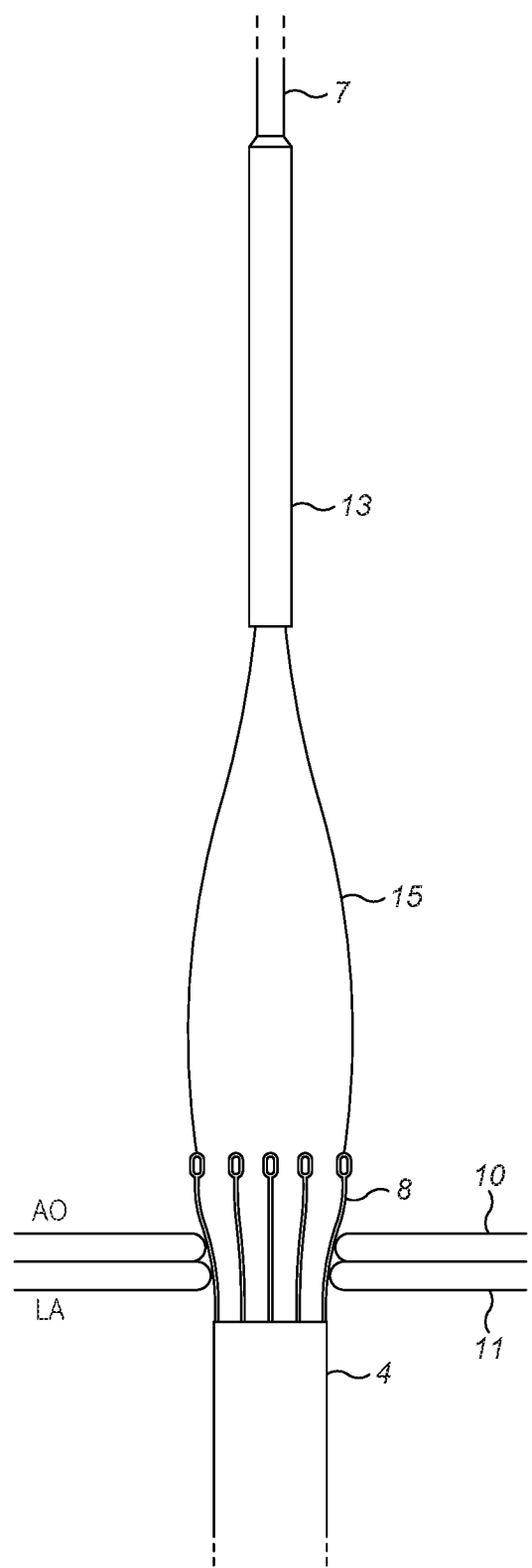

With reference to FIGS. 14a to 14c, the delivery device 7 is pulled back towards the exit point 3 so as to release the ends of the arms 8 of the intracorporeal device 4 (FIG. 14a). The inflatable balloon 15 is inflated using the inflation line (not shown) so as to assist the deployment of the arms 8 (FIG. 14b). The arms 8 deploy until they reach their working position, lying against the aortic wall 10. The balloon 15 is deflated and detached from the intracorporeal device 4 by unscrewing screwing means 22. The distal delivery device 7 may now be removed from patient through exit point 3. The proximal delivery device 6 may also be detached from the intracorporeal device 4 and removed from the patient through entry point.

The present invention has been described in connection to a device delivery process. It is however envisaged that the present invention may be used in connection to a device retrieval process. In the retrieval process, the guide wire and outer sheath are positioned as described above in connection to the delivery process. The distal delivery retrieval device 7 (now distal retrieval device 7) is inserted through the exit point 3 and connected to the distal end 4D of the intracorporeal device 4. The proximal delivery device 7 (now proximal retrieval device 6) is inserted through the entry point 2 and connected to the proximal end 4D of the intracorporeal device 4. The intracorporeal device 4 can be accurately and safely dislodged from the implantation position, and removed from the patient's body.

In another embodiment, the intracorporeal device 4 may be a connector 40 as described in the Applicant's PCT/EP2015/055578, comprising a neck 41 for fluid passage between two compartments LA, AO, a first set of arms 8a destined to lie against the aortic wall 10 in a working configuration, and a second set of arms 8b destined to lie against the roof of the left atrium 11 in a working configuration. This connector 40 is particularly useful when used to anchor a second intracorporeal device such as the pump described above, where said pump does not comprise an integral set of arms (connector).

Figure 15B:
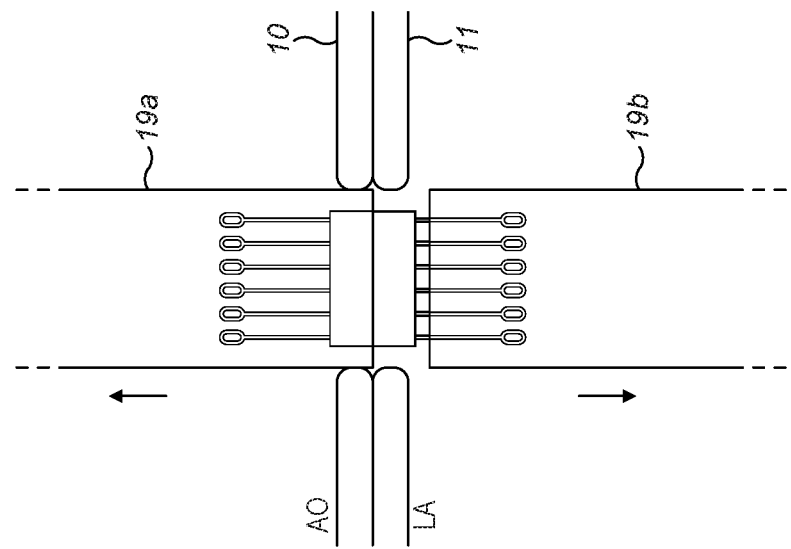
FIGS. 15a to 15d illustrate the delivery and implantation process of an anchor using a delivery catheter with a radial separation mechanism.
Figure 15A:
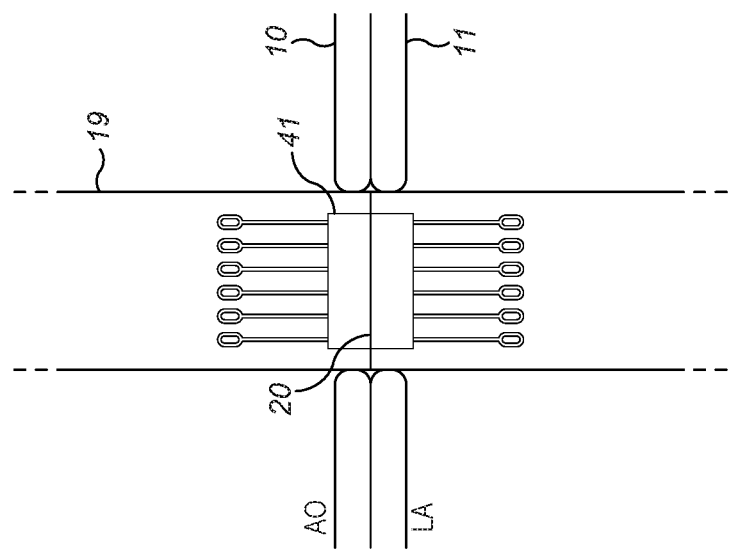
Figure 15C:
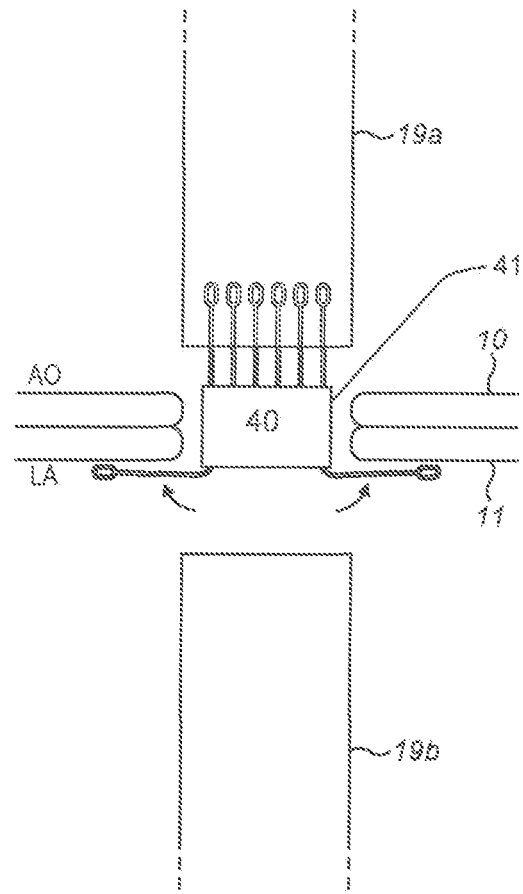
Figure 15D:
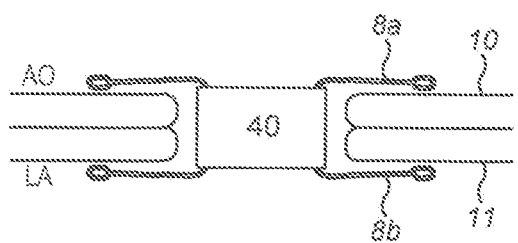

With reference to FIGS. 15a to 15d, the connector 40 is delivered to the target site 5 through a delivery catheter 19 with a radial separation mechanism 20. The neck 41 and the separation line 20 are positioned across the anatomical walls 10, 11 (FIG. 15a). The catheter portions 19a and 19b are separated from each other (FIG. 15b). Proximal catheter portion 19b is pulled back so as to release the atrial arms 8b. The atrial arms 8b expand to lie into their working configuration against the roof of the left atrium 11. Then distal catheter portion 19a is pulled back so as to release the aortic arms 8a. The aortic arms 8a expand to lie into their working configuration against the aortic wall 10. The connector 40 is now implanted into its working configuration and the intracorporeal device 4 (e.g. pump) can now be delivered using the method and devices according to the present invention.

In the method according to the present invention, the anatomical walls are preferably held together by a connector (integral or separate connector) so as to minimise the risk of blood leakage into the inter-compartmental space between the left atrium and the aorta. In addition, the use of the connector is also advantageous in that the walls are less likely to slide or move during the process of implanting an intracorporeal device 4 across the two anatomical walls. Where the intracorporeal device 4 is to be implanted without a connector 40 (integral or separate connector), preferably the method comprises the additional step of suturing and/or stapling the two anatomical walls to each other by means known in the art. Thus, no additional connector device (integral or separate connector) is required.

Thus, from the above description, it can be seen that the present invention provides versatile and accurate method for the delivery or retrieval of an intracorporeal device. The present invention also provides systems and devices for use in said method.

The invention claimed is:

1. A system for delivery of an intracorporeal device to an intracorporeal target site into a patient, the system comprising:
　an intracorporeal device, the intracorporeal device being configured to be delivered through a device delivery pathway which is configured to extend at least from an entry point into the patient to a separate exit point from the patient, and
　at least two delivery devices, including a first, proximal transcatheter delivery device and a second, distal transcatheter delivery device which is separate from the first, proximal transcatheter delivery device,
　the intracorporeal device comprising:
　　a proximal end detachably coupled with the proximal transcatheter delivery device, and a distal end detachably coupled with the distal transcatheter delivery device, so that the intracorporeal device can be manipulated and guided towards the intracorporeal target site from both the entry point and the exit point after insertion into the patient,
　wherein the intracorporeal device is configured to be implanted across one or more anatomical walls at the intracorporeal target site, so that the proximal end of the intracorporeal device is positioned on a proximal side of said one or more anatomical walls and the distal end of the intracorporeal device is positioned on a proximal side of said one or more anatomical walls,
　wherein the proximal transcatheter delivery device is configured to be disposed through the entry point and extends to the proximal end of the intracorporeal device, and the distal transcatheter delivery device is configured to be disposed through the exit point and extends to the distal end of the intracorporeal device.

2. The system according to claim 1, comprising an integrated expandable distal component, said distal component being able to be expanded from a delivery configuration to a working configuration.

3. The system according to claim 2, wherein, in the working configuration, the integrated expanded distal component is arranged and configured to secure the intracorporeal device to the one or more anatomical walls.

4. The system according to claim 2, wherein, in the working configuration, the integrated expanded distal component is a flow diffusor.

5. The system according to claim 2, wherein the integrated expandable distal component comprises a plurality of expandable arms and/or blades.

6. The system according to claim 5, wherein the integrated expandable distal component comprises a membrane extending between the arms and/or blades.

7. The system according to claim 2, further comprising means for assisting the expansion of the integrated expandable distal component into its working configuration.

8. The system according to claim 7, wherein the assisting means comprises an inflatable balloon.

9. The system according to claim 1, comprising a detachable coupling component, said detachable coupling component being able to expand from a delivery configuration to a working configuration.

10. The system according to claim 9, wherein the detachable coupling component comprises a cap and/or a sheath.

11. The system according to claim 9, wherein the detachable coupling component is configured to be coupled to the proximal transcatheter delivery device or the distal transcatheter delivery device.

12. The system according to claim 1, comprising an integrated expandable distal component, said distal component being able to be retracted from a working configuration to a retrieval configuration.

13. The system according to claim 12, wherein, in the retrieval configuration, the integrated expandable distal component is arranged and configured to allow the intracorporeal device to be released from the one or more anatomical walls, after the intracorporeal device has been implanted across said one or more anatomical walls.

14. The system according to claim 1, comprising a detachable coupling component, said detachable coupling component being able to be retracted from a working configuration to a retrieval configuration.

* * * * *